United States Patent [19]
Abbas et al.

[11] Patent Number: 5,591,835
[45] Date of Patent: Jan. 7, 1997

[54] SUBSTITUTED LACTOSE DERIVATIVES

[75] Inventors: Saeed A. Abbas, Vallejo; Falguni Dasgupta, San Leandro, both of Calif.; Darwin Asa, Galesburg, Mich.; John H. Musser, San Carlos; Mina A. Nashed, Alameda, both of Calif.

[73] Assignee: Glycomed Incorporated, Alameda, Calif.

[21] Appl. No.: 189,630

[22] Filed: Feb. 1, 1994

Related U.S. Application Data

[63] Continuation-in-part of Ser. No. 910,709, Jun. 29, 1992, abandoned.

[51] Int. Cl.⁶ .............................. C07H 3/04; C07H 3/06; C07H 15/04
[52] U.S. Cl. .................. 536/4.1; 536/123.1; 536/123.13; 536/124
[58] Field of Search ................................ 536/4.1, 123.1, 536/123.13, 124; 514/53, 61

[56] References Cited

U.S. PATENT DOCUMENTS

| | | | |
|---|---|---|---|
| 4,661,345 | 4/1987 | Tuomanen | 514/8 |
| 4,994,441 | 2/1991 | Neeser | 514/8 |

OTHER PUBLICATIONS

Biochem. Biophys. Res. Comm. 20(1):60–62 (1965).
Carbohydr. Res. 154:93–101 (1986).
J. Am. Chem. Soc. 97(14):4069–4075 (1975).
Methods in Carbohydrate Chemistry, Whistler et al, eds. Academic Press, New York, 1972, pp. 426–429.
Article by Yuen, et al., entitled "Novel Sulfated Ligands for the Cell Adhesion Molecule E–Selectin Revealed by the Neoglycolipid Technology among O–Linked Oligosaccharides on an Ovarian Cystadenoma Glycoprotein" published by *American Chemical Society*, (1992) pp. 9126–9131.
Article by Jain, et al., entitled "A Convenient Synthesis of O–α–L–fucopyranosyl–(1→2)–O–β–D galactopyranosyl–(1→4)–D glucopyranose (2'–O–α–L–fucopyranosyllactose)" published by Elsevier Science Publishers B.V., (1991), pp. c–1–c–3.
Chandrasekaran et al.; Abstract—Abstracts of the 11th International Symposium On Glycoconjugates: (Jun. 30–Jul. 5, 1991).
Hakomori et al., Biochem. Biophys. Res. Commun. 100(4):1578–86 (1981).
Gooi et al.; Nature 292:156–8 (1981).
Shur; J. Biol. Chem. 257(12):6871–8 (1982).
Bird et al.: Devel. Biol. 104:449–60 (1984).
Fenderson et al.: J. Exp. Med. 160:1591–6 (1984).
Gabius et al.,; Anticancer Res. 6:573–8 (1986).
Lis et al.; Ann. Rev. Biochem. 55:35–67 (1986).
Sato et al.: Carb. Res. 155: c6 c10 (1986).
Fenderson et al.; Dev. Biol. 122:21–34 (1987).
Dasgupta et al.; Carb. Res. 177:c13 c17 (1988).
Fenderson et al.; Differentiation 38:124–133 (1988).
Kojima et al.; J. Biol. Chem. 264(34):20159–62 (1989).
Eggens et al.; J. Biol. Chem. 264(16): 9476–84 (1989).
Fernandez–Mayoralas et al, Car. Res. 140:81–91 (Nov. 1985).
Mulligan, et al., "Role of Endothelial–Leukocyte Adhesion Molecule 1 (Elam–1) in Neutrophil–mediated Lung Injury in Rats," J. Clin. Invest, 88:1396–1406 (1991).
Bevilacqua, et al., "Identification of an inductible endothelial–leukocyte adhesion molecule", Proc. Natl. Acad. Sci., USA 84:9238–9242 (1987).
Ma, et al., "Monoclonal Antibody to L–Selectin Attenuates Neutrophil Accumulation and Protects Ischemic Reperfused Cat Myocardium," Circulation, 88:2:649–658 (Aug. 1993).
Entman, et al., "Inflammation in the course of early myocardial ischemia," FASEB Journal, vol. 5, pp. 2529–2537 (Aug. 1991).
Vedder, et al., "Inhibition of leukocyte adherence by anti–CD18 monoclonal antibody attenuates reperfusion injury in the rabbit ear," Proc. Natl. Acad. Sci. USA 87:2643–2646 (Apr. 1990).

(List continued on next page.)

*Primary Examiner*—Michael G. Wityshyn
*Assistant Examiner*—Francisco C. Prats
*Attorney, Agent, or Firm*—Lyon & Lyon

[57] ABSTRACT

Compounds and methods of making them having the following formula are described which bind to selectin receptors and thus modulate the course of inflammation, cancer and related diseases by modulating cell-cell adhesion events:

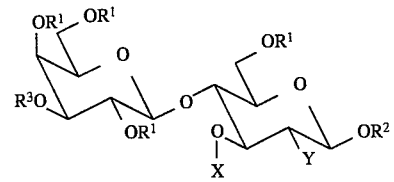

wherein each $R^1$ is independently H or lower alkyl (1–4C);

$R^2$ is H, OH or lower alkyl (1–4C), or a lipophilic group such as a higher alkyl group (5–15C), alkylaryl or one or more additional saccharide residues;

$R^3$ is a negatively charged moiety including $SO_4^{2-}$, $PO_4^{2-}$, or related group;

Y is H or lower alkyl (1–4C); and

X is H or $-CHR_4(CHOR^1)_2CHR^5OR^1$ wherein $R^4$ and $R^5$ are each independently H, lower alkyl (1–4C), or taken together result in a five- or six-membered ring optionally containing a heteroatom selected from the group consisting of O, S, and $NR^1$;

the five- or six-membered ring optionally substituted with one substituent selected from the group consisting of $R^1$, $CH_2OR^1$, $OR^1$, $OOCR^1$, $NR^1_2$, $NHCOR^1$, and $SR^1$ with the proviso that if X represents a hexose substituent $R^3$ and $R^4$, taken together, cannot provide a hexose substituent.

14 Claims, 3 Drawing Sheets

OTHER PUBLICATIONS

Weyrich, et al., "In Vivo Neutralization of P–Selectin Protects Feline Heart and Endothelium in Myocardial Ischemia and Reperfusion Injury," J. Clin. Invest. 91:262–2629 (Jun. 1993).

Yamazaki, et al., "Expression of Intercellular Adhesion Molecule–1 in Rat Heart with Ischemia Reperfusion and Limitation in Infarct Size by Treatment with Antibodies against Cell Adhesion Molecules", Amer. Journal of Path. 143:2:410–418 (Aug. 1993).

Smith, et al., "Leukocyte Adhesion Molecules and Myocardial Ischemia," TMC 1:4:167–170 (1990).

Simpson, "Reduction of Experimental Canine Myocardial Reperfusion Injury by a Monoclonal Antibody (Anti–Mo1, Anti–CD11b) That Inhibits Leukocyte Adhesion," J. Clin. Invest. 81:624–629 (1988).

Winn, "Anti–P–Selectin Monoclonal Antibody Attenuates Reperfusion Injury to the Rabbit Ear," J. Clin. Invest. 92:2042–2047 (Oct. 1993).

Feizi, "Oligosaccharides that mediate mammalian cell–cell adhesion," Current Opinion in Structural Biology 3:701–710 (1993).

Kojima, "Inhibition of Selectin–Dependent Tumor Cell Adhesion to Endothelial Cells and Platelets by Blocking O–Glycosylation of these Cells," Biochem. and Biophys. Res. Comm. 182:3:1288–1295 (1992).

Varki, "Selectins and other mammalian sialic acid–binding lectins," Curr. Opin. in Cell Biology 4:257–266 (1992).

McEver, "GMP–140: A receptor for Neutrophils and Monocytes on Activated Platelets and Endothelium," Journ of Cellular Biochem. 45:156–161 (1991).

Edgington, "How Sweet it is: Selectin Mediating Drugs," Biotechnology, 10:383–389 (1992).

Geng, et al., "Rapid neutrophil adhesion to activated endothelium mediated by GMP–140," Nature, 343:757–760 (1990).

Green, et al., "High Affinity binding of the leucoyte adhesion L–Selectin to 3'–sulphated–lc$^a$ and le$^x$ oligosaccharides and the predominance of sulphate in this interaction demonstrated by binding studies with a series of lipid–linked oligosaccharides," Biochem and Biophys. Res. Comm. 188:1:244–251 (1992).

Foxall, et al., "The Three Members of the Selectin Receptor Family Recognize a Common Carbohydrate Epitope, the Sialyl Lewis$^x$ Oligosaccharide," Journal of Cell Biol., 117:4:895–902 (May 1992).

Yuen, et al., "Sulfated Blood Group Lewis$^a$ A Superior Oligosaccharide Ligand for Human E–Selectin," Journl. Biolog. Chem. 259:3:1595–1598 (1994).

SUBSTITUTED LACTOSE DERIVATIVES

This application is a continuation-in-part of U.S. patent application Ser. No. 07/910,709 filed Jun. 29, 1992, now abandoned.

TECHNICAL FIELD

The invention relates to compounds useful in the treatment of inflammation, allergic reactions, autoimmune diseases, and related conditions. More specifically, the invention concerns substituted lactose that binds to selectin receptors and to pharmaceutical compositions containing them. The present invention is also directed to synthetic methods useful in obtaining these analogs and other lactose derivatives.

BACKGROUND ART

It is now well established that cellular interactions are at least in part mediated by receptor/ligand interactions. One class of receptors is known to recognize the peptide sequence "RGD"; other receptors recognize carbohydrate ligands.

One class of receptors that recognize carbohydrate-based ligands mediates the adhesion of circulating neutrophils to stimulated vascular endothelium. This is a primary event of the inflammatory response and appears to be involved as well in allergic and autoimmune responses. Several receptors have been implicated in this interaction, including a family of putative lectins that includes gp90$^{MEL}$ (Leu8), ELAM-1, and GMP-140 (PADGEM) and (Gong, J. G., et al., *Nature* (1990) 343:757; Johnston, G. I., et al., *Cell* (1989) 56:1033; Geoffrey, J. S., and Rosen, S. D., *J. Cell Biol.* (1989) 109:2463; Lasky, L. A., et al., *Cell* (1989) 56:1045). These lectins have been termed L-SELECTIN, E-SELECTIN, and P-SELECTIN.

E-SELECTIN is perhaps the best characterized of the three selectins. It is particularly interesting because of its transient expression on endothelial cells in response to IL-1 or TNF (Bevilacqua, M. P., et al., *Science* (1989) 243:1160). The time course of this induced expression (2–8 hours) suggests a role for this receptor in initial neutrophil extravasation in response to infection and injury. Furthermore, Bevilacqua et al. (see Bevilacqua, M. P., et al., *Proc. Natl. Acad. Sci. USA* (1987) 84:9238) have demonstrated that human neutrophils or HL-60 cells will adhere to COS cells transfected with a plasmid containing a cDNA encoding for the E-SELECTIN receptor. Information regarding the DNA sequences encoding for endothelial cell-leukocyte adhesion molecules are disclosed within PCT published application WO90/13300 published Nov. 15, 1990.

Recently, several different groups have published papers regarding the ligand for E-SELECTIN. Lowe et al., (1990) Cell, 63:475–484 reported a positive correlation between the E-SELECTIN dependent adhesion of HL-60 cell variants and transfected cell lines, with their expression of the sialyl Lewis x (sLex) oligosaccharide, Neu NAC α2-3-Gal-β1-4(Fuc α1-3)-GlCNAc. By transfecting cells with plasmids containing an α(1,3/1,4) fucosyltransferase, they were able to convert non-myeloid COS or CHO lines into sLex-positive cells that bind in an E-SELECTIN dependent manner. Attempts to block E-SELECTIN dependent adhesion using anti-sLex antibodies were uninterpretable due to the agglutination of the test cells by the antibody. They concluded that one or more members of a family of oligosaccharides consisting of sialylated, fucosylated, lactosaminoglycans are the ligands for the lectin domain of E-SELECTIN. Phillips et al., (1990) Science, 250:1130–1132 used antibodies with reported specificity for sLex to inhibit the E-SELECTIN dependent adhesion of HL-60 or LEC11 CHO cells to activated endothelial cells. Liposomes containing difucosylated glycolipids with terminal sLex structures inhibited adhesion, while those containing nonsialylated Lex structures were partially inhibitory. Walz et al., (1990) Science, 250:1132–1135 were able to inhibit the binding of a E-SELECTIN-IgG chimera to HL-60 cells with a monoclonal antibody directed against sLex or by glycoproteins with the sLex structure, but could not demonstrate inhibition with CD65 or CD15 antibodies. Both groups concluded that the sLex structure is the ligand for E-SELECTIN. U.S. Pat. No. 5,211,937, issued May 18, 1993, assigned to the present assignee and incorporated herein by reference discloses and claims the foregoing minimum tetrasaccharide structure and identifies the groups putatively interactive with the ELAM-1 receptor.

In contrast to E-SELECTIN, the properties of the ligands that bind to L-SELECTIN and P-SELECTIN are not as well worked out. L-SELECTIN appears to bind a sialic acid bearing ligand based on neuraminidase treatment of peripheral lymph node high endothelial venules which inhibits L-SELECTIN recognition. True et al., 1990, J. Cell Biol. 111,2757–2764. Further, other studies using soluble L-SELECTIN in direct binding/inhibition assays suggests that certain carbohydrate moleties may be important ligand components including mannose and fucose, particularly when sulfated or phosphorylated. Imai et al., 1990 J. Cell Biol. 111, 1225–1232. More recent studies suggest that L-Selectin binds to sialyl Lewis X. Foxall, C., et al., *Cell* (1992) 117:895–902.

The ligand to P-SELECTIN is thought to have an epitope related to sialyl Lewis x. This conclusion is based on studies using antibody with this specificity that block P-SELECTIN mediated adhesion of HL-60 cells to activated platelets or COS cells that express P-SELECTIN. Larsen et al. (1990) Cell 63, 467–474. Other experiments have shown that the adhesion of HL-60 cells to P-SELECTIN transfected cells is blocked by the pentasaccharide isolated from milk that has the Lewis$^x$ epitope. Recently, P-Selectin has been shown to bind to sulfatides. Aruffo, A., et al. (1991) Cell, 67:35–44.

Because of the role of selectins in disease, particularly diseases involving unwanted cell-cell adhesion that occurs through selectin-ligand binding on defined cell types, the identification and isolation of novel ligands that would permit the regulation of such selectin-ligand binding is sorely needed.

One of the modes of action of compounds of the invention involves modulating cell-cell adhesion events and is thought to be via selectin-ligand binding. However, it is noteworthy that the additional biological mechanism(s) of action which accounts for the myriad medical activities of compounds of the invention, and derivatives and salts thereof, is not known.

OBJECTS OF THE INVENTION

The invention provides agonists and antagonists which bind to selectin receptors and thus modulate the course of inflammation, cancer and related responses by modulating cell-cell adhesion events. In this aspect, the invention is directed to compounds of the formula:

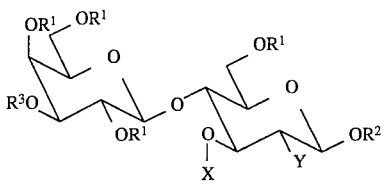

(1)

wherein each $R^1$ is independently H or lower alkyl (1–4C);

$R^2$ is H, lower alkyl (1–4C), a lipophilic group such as a higher alkyl group (5–15C), alkylaryl or one or more additional saccharide residues;

$R^3$ is a negatively charged moiety including $SO^{2-}$, $PO^{3-}$, or related group;

Y is H, OH or lower alkyl (1–4C); and

X is H or, $—CHR^4(CHOR^1)2CHR^5OR^1$ wherein $R^4$ and $R^5$ are each independently H, lower alkyl(1–4C), or taken together result in a five- or six-membered ring optionally containing a heteroatom selected from the group consisting of O, S, and $NR^1$;

said five- or six-membered ring optionally substituted with one substituent selected from the group consisting of $R^1$, $CH_2OR^1$, $OR^1$, $OOCR^1$, $NR^1{}_2$, $NHCOR^1$, and $SR^1$ with the proviso that if X represents a hexose substituent $R^4$ and $R^5$, taken together, cannot provide a hexose substituent.

In another aspect, the invention is directed to a method to synthesize lactose derivatives which method comprises contacting an intermediate of the formula

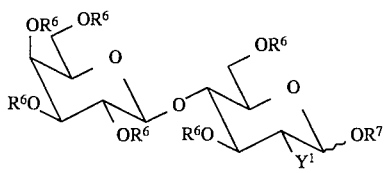

(2)

wherein each $R^6$ is independently H, lower alkyl (1–4C), or a protecting group; and wherein $Y^1$ is H, OH, $OOCR^6$, or $SR^6$;

wherein at least one $R^6$, which is at the position to be substituted, and at most one adjacent $R^6$ is H and all other $R^6$s are protecting groups; and $R^7$ is a protecting group, or a lipophilic group such as a higher alkyl group (5–15C);

with an electrophile-donating moiety to obtain a product wherein the electrophile is substituted for the H of the OH at the position to be substituted.

In other aspects, the invention is directed to pharmaceutical compositions containing the compounds of formula 1 and to methods of treating inflammation using these compositions. In other aspects, the invention is directed to compounds of formula 2 and additional intermediates in the synthesis of selectin binding ligands or other useful lactosyl residue-containing moieties.

FIGURES

MODES OF CARRYING OUT THE INVENTION

Figure 1:
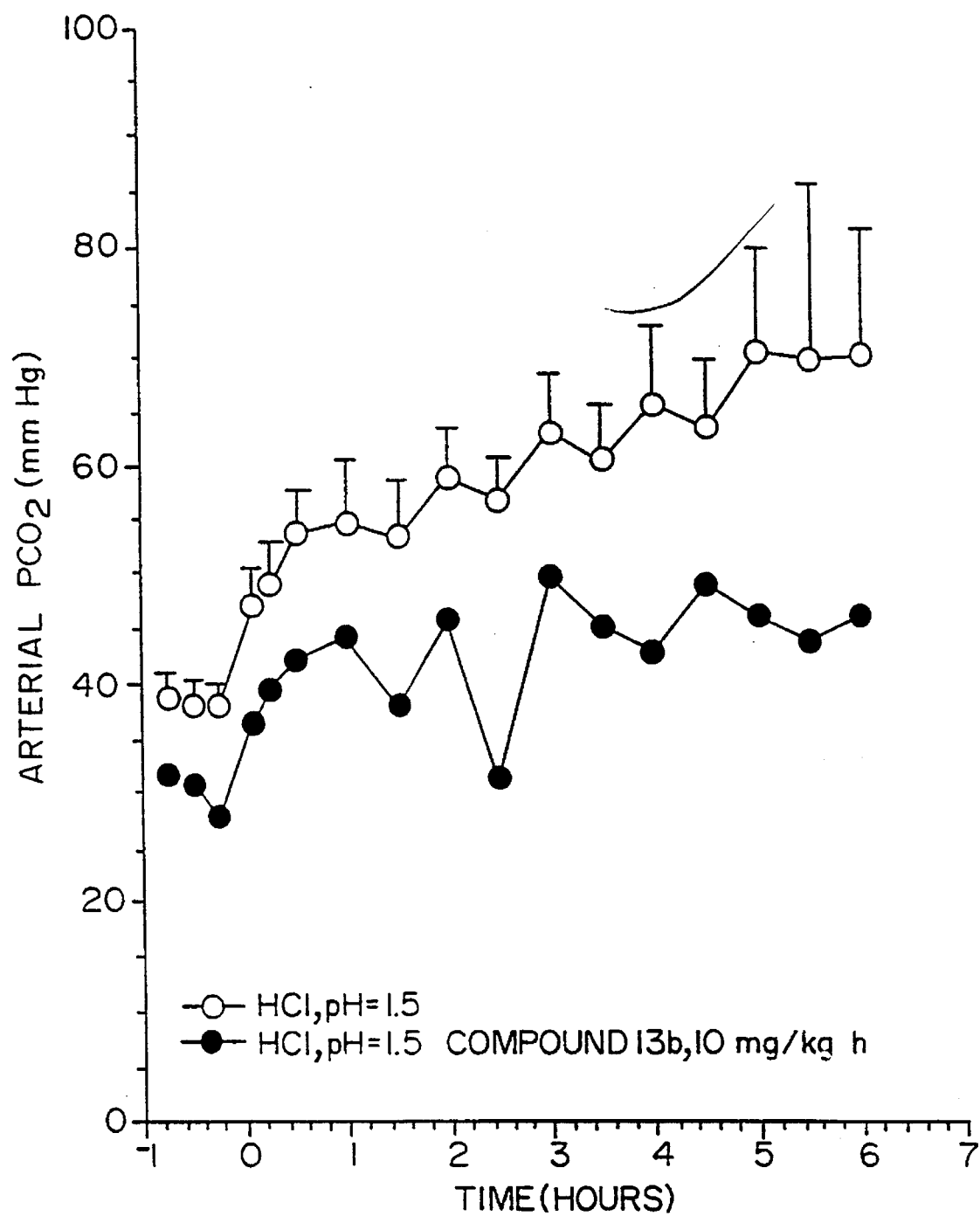
FIG. 1 shows the effect of compound 13b on rabbits in the acute lung injury model.

This application is a continuation-in-part of U.S. patent application Ser. No. 07/910,709 filed Jun. 29, 1992. All patents, patent applications and publications discussed or cited herein are understood to be incorporated by reference to the same extent as if each individual publication or patent application was specifically and individually set forth in its entirety.

The invention provides compounds that are useful in the treatment of inflammation by virtue of their ability to bind to selectin receptors. For example, the role believed to be played by one of the selectin receptors, ELAM-1, in mediating inflammation can be described as follows. Blood vessels are lined with endothelial cells capable of producing the ELAM-1 surface receptor. Lymphocytes circulating in the vessel contain on their surfaces carbohydrate ligands capable of binding to the ELAM-1 receptor. This results in transfer of the lymphocyte through the vessel wall and into the surrounding tissue. While this may have a useful effect in some circumstances, as in cases when the surrounding tissue is infected, excessive transfer of the lymphocytes through the vessel wall and into the tissue may also be excessive and cause unwanted inflammation. While not wishing to be limited by any particular theory, it is believed that the compounds of the present invention which bind the selectin receptors, antagonize the action of the surface ligands on the circulating lymphocytes and thus prevent their transfer through the blood vessel wall to cause inflammation in the surrounding tissue.

For certain cancers to spread throughout a patient's body, a process of cell-cell adhesion or metastasis must take place. Specifically, cancer cells must migrate from their site of origin and gain access to a blood vessel to facilitate colonization at distant sites. A critical aspect of this process is adhesion of cancer cells to endothelial cells that line the blood vessel wall, a step prior to migrating into surrounding tissue. This process can be interrupted by the administration of compounds of the invention which generally aid in blocking cell-cell adhesion. Accordingly, compounds of the invention can be used to retard the spread of cancer cells that display receptors which adhere to a compound of formula 1 or 2.

Assays to Identify Ligands

In their most general form assays for identifying lactose derivatives that act as selectin ligands involve contacting the appropriate selectin, L-SELECTIN, E-SELECTIN, or P-SELECTIN, with a putative ligand and measuring its binding properties.

Several assays are available to measure the capacity of a compound to bind to L-SELECTIN, E-SELECTIN, or P-SELECTIN, and such assays are well known in the art. For example, both the selectin and the putative ligand may be in solution for a time sufficient for a complex of the selectin and ligand to form, followed by separating the complex from uncomplexed selectin and ligand, and measuring the amount of complex formed. Alternatively, the amount of uncomplexed selectin or compound could be measured.

A second and preferred assay format consists of immobilizing either the selectin or the putative ligand on a solid surface, and forming the selectin-ligand complex thereon by contacting the immobilized reagent with the non-immobilized reagent. The selectin-ligand complex is separated from uncomplexed reagents, and the amount of complex formed can be determined by measuring the amount of the non-immobilized reagent present in the complex. For example, the putative ligand can be affixed to a microtiter well, followed by adding the desired selectin to the well and measuring the amount of selectin bound to the ligand.

A variation of the above assay is to genetically engineer cells to express high levels of L-SELECTIN, E-SELECTIN, or P-SELECTIN on their surface, and to use the cells in lieu of purified selectin. Radiolabeled COS cells have been used in this type of assay, and can be transfected with cDNA that encodes for L-SELECTIN, E-SELECTIN or P-SELECTIN. After the cells have had a sufficient time to adhere to the ligand coated microtiter well, non-adherent cells are removed and the number of adherent cells determined. The number of adherent cells reflects the capacity of the ligand to bind to the selectin.

Representative of the application of this type of assay is the identification of E-SELECTIN ligands. For example, a complete cDNA for the ELAM-1 receptor was obtained by PCR starting with total RNA isolated from IL-1 stimulated human umbilical vein endothelium. The resulting cDNA was inserted into the CDM8 plasmid (see Aruffo, A., and Seed, B., *Proc. Natl. Acad. Sci. USA* (1987) 84:8573) and the plasmid amplified in *E. coli*. Plasmid DNA from individual colonies was isolated and used to transfect COS cells. Positive plasmids were selected by their ability to generate COS cells that support HL-60 cell adhesion. DNA sequencing positively identified one of these clones as encoding for ELAM-1 (Bevilacqua, M. P., et al., *Science,* (1989) 243:1160; Polte, T., et al., *Nucleic Acids Res.* (1990) 18:1083; Hession, C., et al., *Proc. Natl. Acad. Sci. USA* (1990) 87:1673). These publications are incorporated herein by reference for their disclosure of ELAM-1 and genetic material coding for its production. The complete nucleotide sequence of the ELAM-1 cDNA and predicted amino acid sequence of the ELAM-1 protein are given in the above cited article by Bevilacqua et al., which DNA and amino acid sequences are incorporated herein by reference (see also published PCT patent application WO90/13300 which was published Nov. 15, 1990, which is incorporated herein by reference).

A full length cDNA encoding ELAM-1 was obtained by 35 cycles of the polymerase chain reaction with 1 μg of total RNA extracted from IL-1 stimulated human umbilical vein endothelial cells, utilizing primers complementary to the untranslated flanking sequences SEQ ID NO: 1 and SEQ ID NO: 2. The 2Kb insert generated by this method was gel purified, directionally cloned into the mammalian expression vector, CDM8 that had been modified by the insertion of a SalI site into the polylinker, and grown in *E. coli* (MC1061/p3). Plasmids were isolated from individual colonies and used to transfect COS cells. Putative E-SELECTIN encoding plasmids were selected based on the ability of these transfected COS cells to support HL-60 cell adhesion 72 hours post-transfection.

A positive cDNA whose sequence corresponded to the published sequence of E-SELECTIN with two nucleic acid substitutions was used in all experiments. COS cells were transfected with 1 μg of this plasmid DNA per $3.5-5.0 \times 10^5$ cells, with 400 μg/ml DEAE-dextran and 100 μM chloroquine for 4 h, followed by a brief exposure to 10% DMSO in PBS. Cells were metabolically radiolabeled overnight with carrier free $^{32}PO_4$ and harvested in PBS supplemented with 0.02% azide and 2 mM EDTA at 72 hours post-transfection for use in cell adhesion studies.

E-SELECTIN transfected COS cells produced by the above method may be used to assay for glucuronyl glycolipid ligands. Similarly, COS cells may be transfected with cDNAs that encode L-SELECTIN and/or P-SELECTIN. The production and characterization of L-SELECTIN IgG chimera constructs have been previously described by Watson S. R. et al., (1990) J. Cell Biol. 110: 2221–2229. This chimera contains two complement binding domains, consistent with its natural expression. See Watson S. R. et al., (1991) J. Cell Biol. 115: 235–243. P-SELECTIN chimera was constructed in a similar manner as described by Walz, G., et al (1990) Science 250, 1132–1135, and Aruffo, A. et al. (1991) Cell, 67, 35–44, respectively. The chimeras may be expressed in a suitable host cell, for example, 293 cells and purified. Protein A affinity chromatography is the preferred method of purification. E-SELECTIN and P-SELECTIN may be constructed with truncated complement binding domains to standardize the size of the chimeras and to facilitate their secretion. A variation of the above assay is to genetically engineer cells to express high levels of L-SELECTIN, E-SELECTIN, or P-SELECTIN on their surface, and to use the cells in lieu of purified selectin. Radiolabeled COS cells have been used in this type of assay, and can be transfected with cDNA that encodes for L-SELECTIN, E-SELECTIN or P-SELECTIN. After the cells have had a sufficient time to adhere to the ligand coated microtiter well, non-adherent cells are removed and the number of adherent cells determined. The number of adherent cells reflects the capacity of the ligand to bind to the selectin.

Thus, any candidate compound of the formula 1 may be verified to bind selectin receptors by a positive result in the foregoing assays. These assays provide a simple screen for determining the relative effectiveness of the various members of the group consisting of compounds of formula 1.

Nontherapeutic uses of Compounds of Formula 1

In addition to their use in treating or preventing inflammation as is further described hereinbelow, the compounds of formula 1 are useful in diagnostic and preparatory procedures both in vitro and in vivo.

Compounds of formula 1 may be conjugated to solid substrates and used for the purification of selectin receptor protein from biological samples. This is conducted most conveniently by arranging the coupled substrate as an affinity chromatography column and applying a sample putatively containing the selectin receptor protein to the affinity column under conditions wherein the selectin receptor protein is adsorbed whereas contaminating materials are not. The selectin receptor protein is then subsequently eluted, for example, by adjusting the eluent solution to contain competing amounts of the compound of formula 1 or by adjusting pH or salt parameters. Techniques for affinity purification are well understood, and routine optimization experiments will generate the appropriate conditions for conduct of the procedure.

The compounds of formula 1 are also useful as detection reagents to determine the presence or absence of selectin or related carbohydrate-binding receptor ligands. For use in such diagnostic assays, a biological sample suspected to contain selectin receptor protein or a receptor protein closely related thereto is treated with the compound of formula 1 under conditions wherein complexation occurs between the receptor protein and the formula 1 compound, and the formation of the complex is detected. A wide variety of protocols may be utilized in such procedures, analogous to protocols applied in immunoassays. Thus, direct assay wherein the amount of complex formed is directly measured may be utilized; alternatively, competition assays may be used wherein labeled selectin receptor protein is supplied along with, and in competition with, the biological sample.

In some forms of the assay, it is convenient to supply the compounds of formula 1 in labeled form so that the complex is detected directly; in alternate procedures, the complex may be detected by size separations, secondary labeling reagents, or other alternate means. Suitable labels are known in the art, and include radioactive labels, fluorescent labels, enzyme labels, chromogenic labels, or composites of these approaches.

The compounds of formula 1 may also be used as competitive diagnostic reagents to detect the quantity of selectin receptor-binding components, such as surface ligands, in biological fluids. For the conduct of such assays, the compounds of formula 1 are labeled as described above and mixed with the biological sample and contacted with the appropriate receptor protein; the diminution of binding of the labeled compound of formula 1 to selectin receptor in the presence of biological sample is then determined.

The compounds of formula 1 may also be used in imagining studies in vivo to determine the location of selectin receptors in situ. For use in such assays, the compounds of formula 1 are supplied with labels which can be detected by in vivo imaging techniques, such as scintigraphic labels including indium 111, technetium 99, iodine 131, and the like.

Techniques for coupling compounds such as those of formula 1 to labels, chromatographic supports, or other moieties useful in employing the compounds in the relevant procedures are well understood in the art.

Antibodies may also be prepared to the compounds of formula 1 by coupling these compounds to suitable carriers and administering the coupled materials to mammalian or other vertebrate subjects in standard immunization protocols with proper inclusion of adjuvants. Suitable immunogenic carriers include, for example, Keyhole Limpet Hemocyanin (KLH), tetanus toxoid, various serum albumins such as bovine serum albumin (BSA) and certain viral proteins such as rotaviral VP6 protein. These coupled materials are then administered in repeated injections to subjects such as rabbits, rats or mice and antibody titers monitored by standard immunoassay techniques. The resulting antisera may be used per se or the antibody-secreting cells generated by the immunization may be immortalized using standard techniques and used as a source of monoclonal preparations which are immunoreactive with the compounds of formula 1. The resulting antibodies are useful in assay systems for determining the presence and/or amount of the relevant formula 1 compound. Such assays are useful in monitoring the circulating levels of compounds of formula 1 in therapeutic treatments such as those described below.

Administration in Anti-inflammatory Protocols

The compounds of the invention are administered to a subject in need thereof for prophylactically preventing inflammation or relieving it after it has begun. "Treating" as used herein means preventing or ameliorating inflammation and/or symptoms associated with inflammation. The compounds are preferably administered with a pharmaceutically acceptable carrier, the nature of the carrier differing with the mode of administration, for example, oral administration, usually using a solid carrier and I.V. administration using a liquid salt solution carrier. Typically, injectable compositions are prepared as liquid solutions or suspensions; solid forms suitable for solution in, or suspension in, liquid vehicles prior to injection may also be prepared. The compounds may also be emulsified or the active ingredient encapsulated in liposome vehicles.

Suitable vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, for example, *Remington's Pharmaceutical Sciences,* Mack Publishing Company, Easton, PA, 17th edition, 1985. Formulations may employ a variety of excipients including, for example, pharmaceutical grades of mannitol, lactose, starch, magnesium stearate, sodium saccharin cellulose, magnesium carbonate, and the like. Oral compositions may be taken in the form of solutions, suspensions, tablets, pills, capsules, sustained release formulations, or powders. Particularly useful is the administration of the subject ligand molecules directly in transdermal formulations with permeation enhancers such as DMSO. Other topical formulations can be administered to treat dermal inflammation. In addition, transmucosal administration may be effected using penetrants such as bile salts or fusidic acid derivatives optionally in combination with additional detergent molecules. These formulations are useful in the preparation of suppositories, for example, or nasal sprays. For suppositories, the vehicle composition will include traditional binders and carriers, such as polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Typically, the compositions of the instant invention will contain from less than 1% to about 95% of the active ingredient, preferably about 10% to about 50%. Preferably, between about 10 mg and 50 mg will be administered to a child and between about 50 mg and 1000 mg will be administered to an adult. The frequency of administration will be determined by the care given based on patient responsiveness. Other effective dosages can be readily determined by one of ordinary skill in the art through routine trials establishing dose response curves.

In determining the dose to be administered, it will be noted that it may not be desirable to completely block all selectin receptors of a particular type. In order for a normal healing process to proceed, at least some of the white blood cells or neutrophils must be brought into the tissue in the areas where any wound, infection or disease state is occurring. The amount of the selectin ligands administered as blocking agents must be adjusted carefully based on the particular needs of the patient while taking into consideration a variety of factors such as the type of disease that is being treated.

The compounds of the present invention are useful to treat a wide range of diseases, for example autoimmune diseases such as rheumatoid arthritis and multiple sclerosis. The compositions of the invention are applicable to treat any disease state wherein the immune system turns against the body causing the white cells to accumulate in the tissues to the extent that they cause tissue damage, swelling, inflammation and/or pain.

Reperfusion injury is a major problem in clinical cardiology. Therapeutic agents that reduce leukocyte adherence in ischemic myocardium can significantly enhance the therapeutic efficacy of thrombolytic agents. Thrombolytic therapy with agents such as tissue plasminogen activator or streptokinase can relieve coronary artery obstruction in many patients with severe myocardial ischemia prior to irreversible myocardial cell death. However, many such patients still suffer myocardial neurosis despite restoration of blood flow. This "reperfusion injury" is known to be associated with adherence of leukocytes to vascular endothelium in the ischemic zone, presumably in part because of activation of platelets and endothelium by thrombin and cytokines that makes them adhesive for leukocytes (Romson et al., *Circulation* 67:1016–1023, 1983). These adherent leukocytes can migrate through the endothelium and ischemic myocardium just as it is being rescued by restoration of blood flow.

There are a number of other common clinical disorders in which ischemia and reperfusion results in organ injury mediated by adherence of leukocytes to vascular surfaces, including strokes; mesenteric and peripheral vascular disease; organ transplantation; and circulatory shock (in this case many organs might be damaged following restoration of blood flow).

Formulations of the present invention might also be administered to prevent the undesirable after effects of tissue damage resulting from heart attacks. When a heart attack occurs and the patient has been revived, such as by the application of anticoagulants or thrombolytic (e.g., tPA), the endothelial lining where a clot was formed has often suffered damage. When the antithrombotic has removed the clot, the damaged tissue beneath the clot and other damaged tissue in the endothelial lining which has been deprived of oxygen become activated. The activated endothelial cells then synthesize selectin receptors, for example ELAM-1 receptors, within hours of the cells being damaged. The receptors are extended into the blood vessels where they adhere to glycolipid ligand molecules on the surface of white blood cells. Large numbers of white blood cells are quickly captured and brought into the tissue surrounding the area of activated endothelial cells, resulting in inflammation, swelling and necrosis which thereby decreases the likelihood of survival of the patient.

In addition to treating patients suffering from the trauma resulting from heart attack, patients suffering from actual physical trauma could be treated with formulations of the invention in order to relieve the amount of inflammation and swelling which normally result after an area of the body is subjected to severe trauma. Other conditions treatable using formulations of the invention include various types of arthritis and adult respiratory distress syndrome. After reading the present disclosure, those skilled in the art will recognize other disease states and/or symptoms which might be treated and/or mitigated by the administration of formulations of the present invention.

Applications of Compounds of Formula 2

The compounds of formula 2 are intermediates in the preparation of compounds which contain a lactosyl unit. Notably, the compounds of formula 2 are useful in the preparation of compounds of formula 1 whose use is described hereinabove. In addition to the compounds of formula 1, alternative compounds containing a lactose residue may also be prepared, such as:

4-O-(3-O-carbonymethyl-β-D-galactopyranosyl)-3-O-[2R,S)-glyceryl]-D-glucopyranose;

4-O-(3-O-carbonymethyl-β-D-galactopyranosyl)-3-O-[2R,S)-2,3-dideoxy-2,3-difluoro-propyl]-D-glucopyranose;

4-O-[3-O-{(1R,S)-1-(carboxy)ethyl}-β-D-galactopyranosyl]-3-O-[(2R,S)-glycosyl]-D-glucopyranose;

4-O-[3-O-{(1R,S)-1-(carboxy)ethyl}-β-D-galactopyranosyl]-3-O-(α-L-fucopyranosyl)-D-glucopyranose;

4-O-[3-O-(α-Neu5Ac)-β-D-galactopyranosyl]-3-O-[(2R,S)-glyceryl]-D-glucopyranose;

4-O-[3-O-(α-Neu5Ac)-β-D-galactopyranosyl]-3-O[(2R,S))-2,3-dideoxy-2,3-difluoro-propyl]-D-glucopyranose.

Multivalent Forms of the Receptor Binding Ligands

The affinity of the ligands of the invention for receptor can be enhanced by providing multiple copies of the ligand in close proximity, preferably using a scaffolding structure that is, for example, provided by a carrier moiety. It has been shown that provision of such multiple valence structures with optimal spacing between the moieties dramatically improves binding to receptor. For example, Lee, R. et al., *Biochem* (1984) 23:4255, showed that providing multivalent forms of lactose inhibited labeled ASOR binding to mammalian hepatocytes much more effectively when the lactose was supplied as a multivalent entity; the $IC_{50}$ dropped from 500 μM for a single valent lactose to 9 for a divalent lactosyl compound to 4 for a trivalent lactosyl compound, and with ideal or optimal spacing between the three lactose moieties to 0.007 μM.

The multivalency and spacing can be controlled by selection of a suitable carrier moiety. Such moieties include molecular supports which contain a multiplicity of functional groups that can be reacted with functional groups associated with the ligands of the invention. A particularly preferred approach involves coupling of the lactose-derived ligands of the invention to amino groups of the carrier through reductive amination. Reductive amination is a particularly convenient way to couple aldehyde moieties to free amino groups by first forming the Schiff base and then treating the conjugate with a reducing agent, such as a hydride reducing agent. Typically, the amino group-bearing carrier is mixed with the carbohydrate moiety at about pH 9 and allowed to form the Schiff base; the solvents are typically evaporated and reducing agent is added at high pH to complete the reaction.

Particularly convenient carrier moieties to obtain multivalent forms of the invention ligands include proteins and peptides, particularly those containing lysyl residues which have ε-amino groups available for binding. It is also useful to include in the peptide or protein at least one tyrosine residue, as this offers a convenient site for labeling, for example with radioactive iodine. A particularly convenient carrier to obtain a trivalent couple is the peptide Lys-Tyr-Lys. Complete reaction of the ligands of the invention with the free amino groups on this peptide results in a trivalent moiety. Thus, compounds of the invention of the formula:

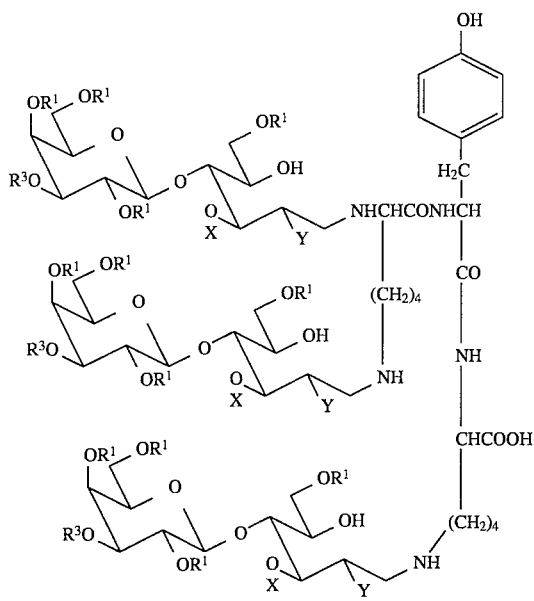

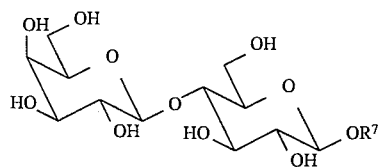

wherein X, Y, and $R^1$, and $R^3$ are as defined above, and illustrate the multivalent compounds of the invention. Of course, a variety of carriers can be used, including proteins such as BSA or HSA, a multiplicity of peptides including, for example, pentapeptides, decapeptides, pentadecapeptides, and the like. Preferably, the peptides or proteins contain the desired number of amino acid residues having free amino groups in their side chains; however, other functional groups, such as sulfhydryl groups or hydroxyl groups can also be used to obtain stable linkages. For example, the carbohydrate ligands of the invention may be oxidized to contain carboxyl groups at the reducing terminus which can then be derivatized with either free amino groups to form amides or with hydroxyl groups to form esters.

Preparation of the Compounds of Formula 1

The compounds of the invention of Formula 1 may be synthesized using an intermediate of Formula 2. The intermediate of Formula 2, in one embodiment, can be prepared directly from D-lactose using standard procedures. In this conversion, D-lactose is converted to the octaacetate in crystalline form, in over 95% yield in the method described by Hudson, C., and Kuns, A., *J Am Chem Soc* (1925) 47:2052. The octaacetate is, in turn, converted in more than 90% yield by the method of Hudson, C. (supra) or of Fischer, E. and Fischer, H., Ber (1910) 43:2521 to the corresponding lactosyl bromide, also a crystalline compound. The protected lactosyl bromide is converted by the method of Jansson, K., et al., *J Org Chem* (1988) 53:5629, in over 60% yield to the corresponding acylated trimethylsilyl ethyl lactose, which can be deprotected by deacylation in quantitative yield to obtain 2-(trimethylsilyl)ethyl lactoside, 2-(trimethylsilyl)ethyl β-D-galactopyranosyl-β-D glucopyranoside. Alternative protecting groups at position 1 of the disaccharide may also be used.

This precursor of the compounds of Formula 2 is of the formula:

wherein $R^7$ is a protecting group, preferably SE or Bn or a lipophilic group such as a higher alkyl group (5–15C), wherein SE represents —CH$_2$CH$_2$SiMe$_3$ and Bn is benzyl.

Reaction Scheme 1 outlines the formation of one embodiment of the compounds of Formula 2 from this intermediate, where Bz represents benzoyl.

In step 1 of the reaction scheme, the protected lactose, e.g., the trimethylsilyl ethyl derivative, is treated with an excess of 2,2-dimethoxypropane and dry camphor sulfonic acid is added to the reaction mixture which is stirred for 2–3 days at about room temperature. A suitable base, such as triethylamine is added and stirring continued for 10–20 minutes; the mixture is then concentrated to dryness and the base removed. In the case of benzyl lactoside, the method employed is that of D. Beith-Halahmi et al., *Carbohydr. Res.*, (1967) 5:25, wherein benzyl lactoside is boiled for 3–4 hours in a large excess of dry acetone containing 4-toluene sulfonic acid. The reaction mixture is worked up using standard procedures to recover the product 6 a, b (or 19). This intermediate is then benzoylated under suitable conditions using, for example, benzoyl chloride to obtain the intermediate compound shown in reaction scheme as 7 a, b (or 20).

The intermediate 7 a, b (or 20) may then be further derivatized at the free hydroxyl at the 3-position of the glucoside residue or this position may be protected and the compound deprotected at positions 3 and 4 of the galactosyl residue and further derivatized at position 3. Position 4 of the galactosyl residue is relatively unreactive. A typical scheme for utilization of this key intermediate 7 a, b (or 20) is shown in Reaction Scheme 2A. (In this scheme, Bz is benzoyl (PhCO—) and Bn is benzyl (PhCH$_2$—).

Reaction Scheme 1

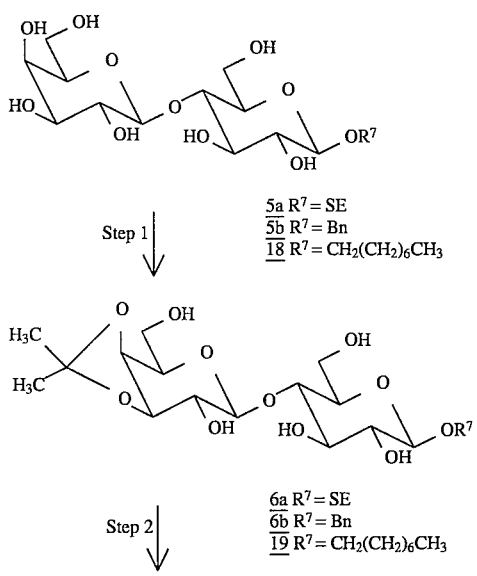

13
-continued
Reaction Scheme 1

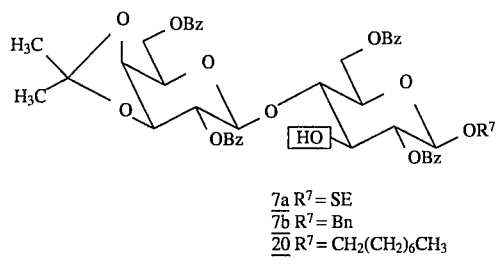

7a R⁷ = SE
7b R⁷ = Bn
20 R⁷ = CH₂(CH₂)₆CH₃

Reaction Scheme 2A

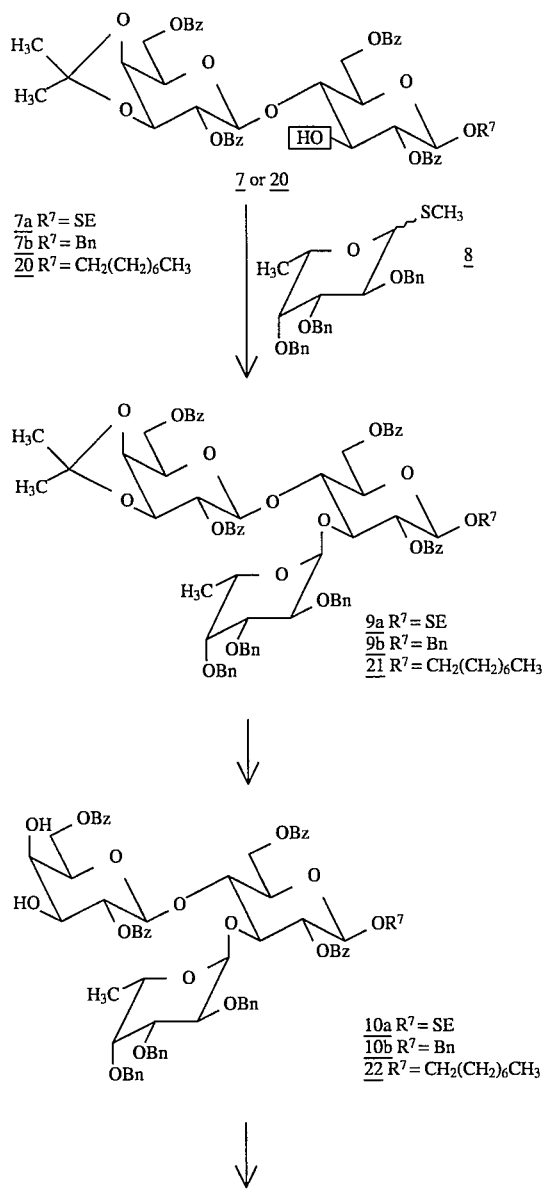

7a R⁷ = SE
7b R⁷ = Bn
20 R⁷ = CH₂(CH₂)₆CH₃

9a R⁷ = SE
9b R⁷ = Bn
21 R⁷ = CH₂(CH₂)₆CH₃

10a R⁷ = SE
10b R⁷ = Bn
22 R⁷ = CH₂(CH₂)₆CH₃

14
-continued
Reaction Scheme 2A

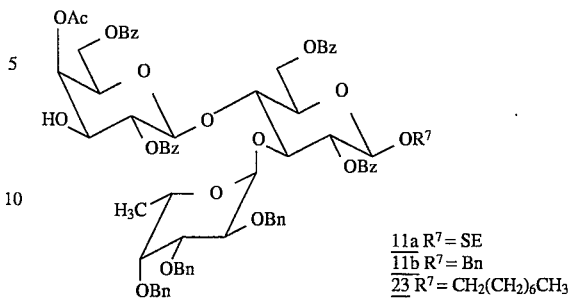

11a R⁷ = SE
11b R⁷ = Bn
23 R⁷ = CH₂(CH₂)₆CH₃

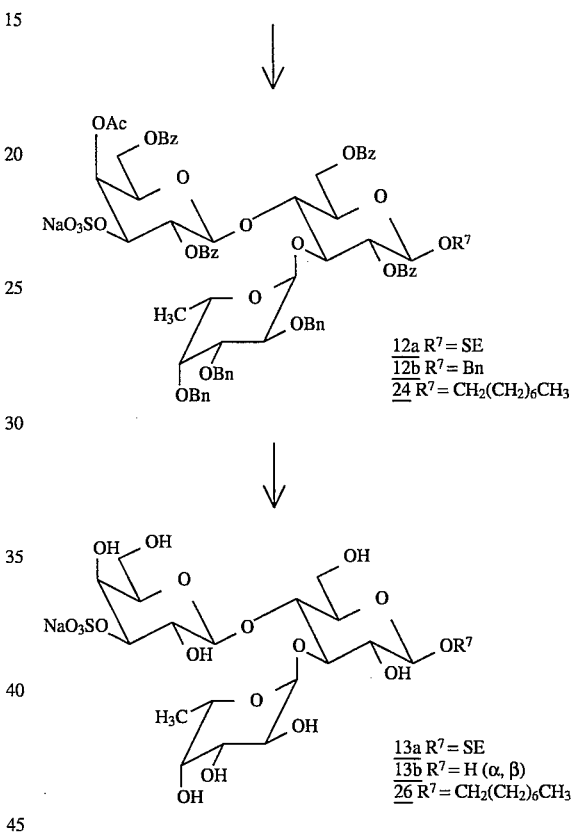

12a R⁷ = SE
12b R⁷ = Bn
24 R⁷ = CH₂(CH₂)₆CH₃

13a R⁷ = SE
13b R⁷ = H (α, β)
26 R⁷ = CH₂(CH₂)₆CH₃

As shown in Reaction Scheme 2A, the intermediate 7 a, b (or 20) is converted in two steps to intermediate 10 a, b (or 22) by treatment under suitable conditions with protected methyl 1-thio-L-fucoside. The reaction is conducted in a nonaqueous aprotic solvent in the presence of cupric bromide, tetrabutylammonium bromide and molecular sieve. (S. Sato, et al., *Carbohydr. Res.* (1986) 155:C6). The resultant compound shown as 10 a, b is then selectively acetylated at position 4 of D-galactopyranosyl residue by the way of its 3,4- orthoester, according to literature procedure, without isolation of the intermediate (R. U. Lemieux and H. Drigwez, *J. Amer. Chem. Soc.*, (1975) 97:4069) to give intermediate 11 a, b (or 23). Sulfation of intermediate 11 a, b (or 23) produces intermediate 12 a, b (or 24) which is deacylated and hydrogenated to yield the final product 13 a, b (or 26), a selectin ligand.

In another embodiment of the instant invention, shown in reaction scheme 2B, intermediates 11 a, b or 23 may be phosphorylated to yield intermediates 14a, b or c respectively, which upon deacylation and hydrogenation yields the final product 15a, b or c. These compounds would be expected to act as selectin ligand.

In another embodiment of the instant invention, shown in reaction scheme 3, intermediate 29, generated via intermediates 27 and 28 from 19, may be sulphated or phosphorylated to yield intermediate 80a or b, respectively which upon deacylation and hydrogenation yields the final product 31a or b, respectively. These compounds would be expected to act as a selectin ligand.

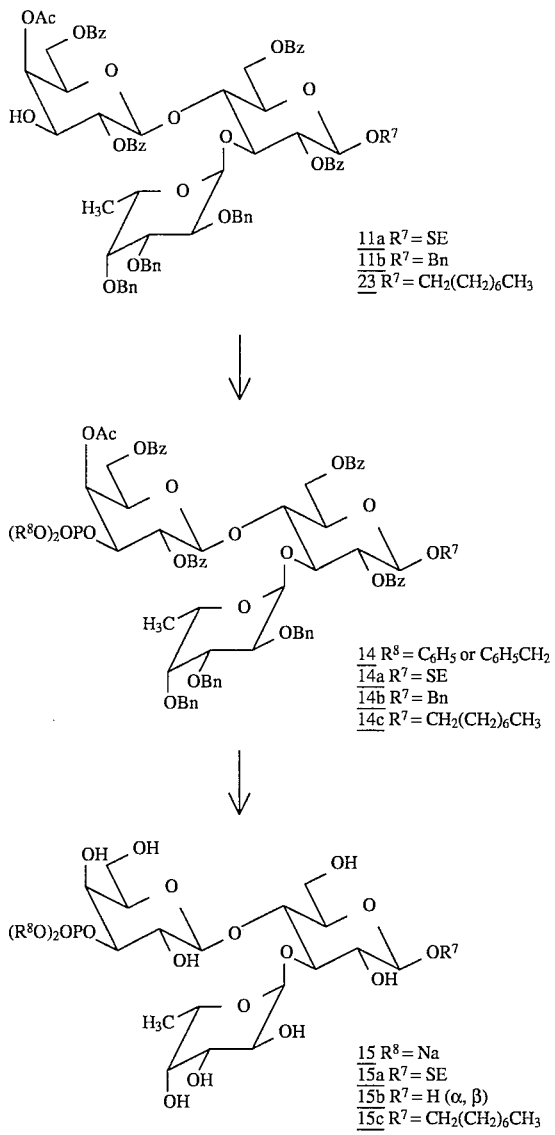

Reaction Scheme 2B

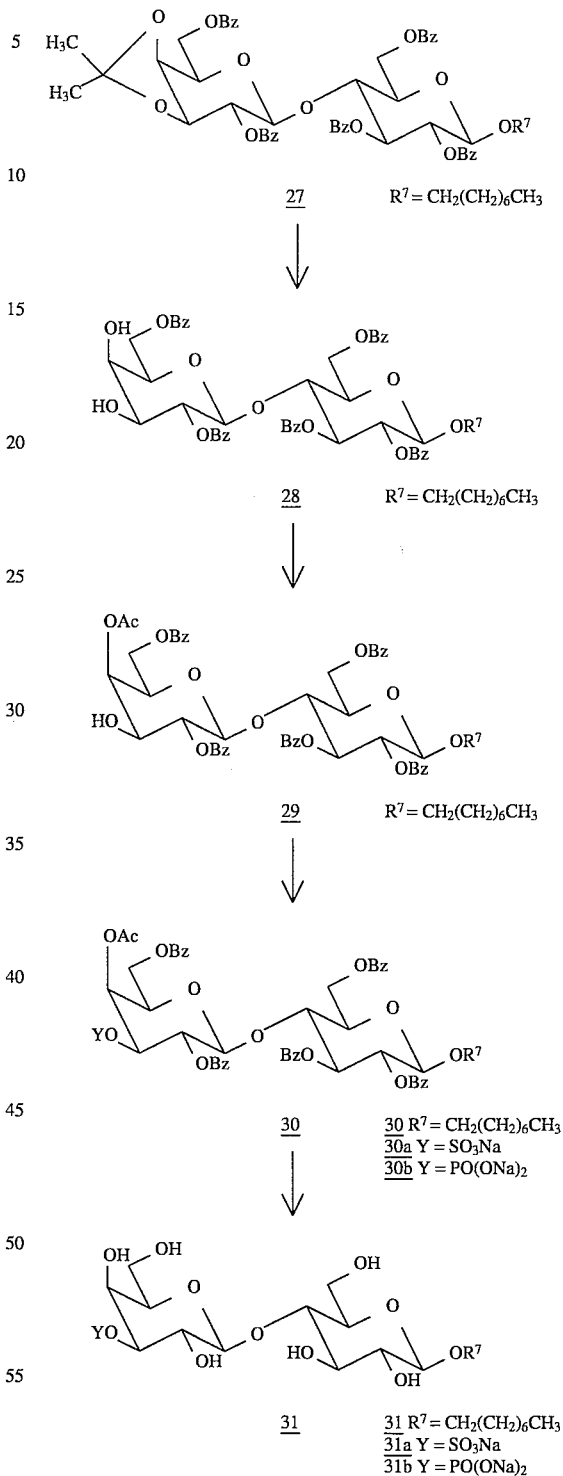

Reaction Scheme 3

Compounds of the Invention and Preferred Embodiments

As used herein, alkyl (1–6C) refers to a saturated straight or branched chain or cyclic hydrocarbyl residue containing 1–6C; lower alkyl is similarly defined but containing only 1–4C, higher alkyl is similarly defined but containing 5–15C.

As used herein, alkylaryl is of the formula $(CH_2)_m$-Ar wherein m is 1–10 and Ar is a mono- or bicyclic aromatic residue optionally containing one or more heteroatoms. Typical embodiments of Ar include phenyl, naphthyl, quinolyl, pyridyl, pyrimidinyl, benzthiazoyl, benzimidazoyl, and the like.

$R^7$ is a protecting group or a lipophilic group suitable for saccharide residues. Typical protecting groups include benzyl, benzoyl, various silylalkyl groups, such as trimethylsilylethyl (SE), and the like, and lipophilic groups such as a higher alkyl group (5–15C) as defined above.

Exemplary compounds of formula 1 of the invention are those wherein $R^3$ is $SO^3$, $PO^1$, or other similar charged moiety.

Additional exemplary compounds of formula 1 include those wherein X is:
6-methyl-3,4,5-trihydroxypyran-2-yl,
6-acetyl-3,4,5,trihydroxypyran-2-yl,
6-propylamido-3,4,5,trihydroxypyran-2-yl,
6-propylamido-2,3,4-trimethoxypyran-2-yl,
6-ethyl-2,3-dihydroxy-4-methoxypyran-2-yl,
6-N-ethylamino-2-hydroxy-3,4-ethoxypyran-2-yl,
3,4,5-tri-n-propyloxypyran-2-yl,
3,4,5-trihydroxypyran-2-yl,
2,3,4-trimethoxyfuran-2-yl,
2,3-dihydroxy-4-methoxyfuran-2-yl,
2-hydroxy-3,4-ethoxyfuran-2-yl,
3,4,5-tri-n-propyloxyfuran-2-yl, and
3,4,5-trihydroxyfuran-2-yl;
or wherein both $R^5$ and $R^6$ are H and all $R^1$ in X are H or methyl;
or wherein X is 2,3,4-trihydroxybenzoyl,
or wherein X is H.

Thus, particularly preferred compounds of formula 1 are those wherein all $R^1$ are H or methyl, Y is H, OH, $OCH_3$ or OAc; and/or X is $-CH_2(CHOH)_3H$, 3,4,5-trihydroxypyran-2-yl, 3,4,5-trihydroxy-6-methylpyran-2-yl, 3,4,5-trimethoxypyran-2-yl, 3,4,5-trimethoxy-6-methylpyran-2-yl, 3,4,5-trihydroxyfuran-2-yl, 3,4,5-trimethoxyfuran-2-yl, 2,3,4-trihydroxybenzoyl, or 2,3,4-trihydroxynaphthoyl; and $R^3$ is $SO^3$, $PO^3$, or other similar charged moiety.

Most preferred of the compounds of formula 1 are those wherein all $R^1$ are H, $R^2$ is H, or $-CH_2(CH_2)_6CH_3$, Y is H, $OR^1$, or lower alkyl.

For those compounds of formula 2 which represent intermediates preferred forms are those wherein the protecting groups represented by $R^6$ are benzyl or benzoyl, the protecting group represented by $R^7$ is trimethylsilylethyl or benzyl, or a lipophilic group such as a higher alkyl group (5–15C), and wherein $Y^1$ is H, $OR^6$ wherein $R^6$ is benzyl or benzoyl as set forth above, and where the free hydroxyl group(s) is at position 3 of the glucosyl moiety or positions 3 and 4 of the galactosyl moiety. An additional preferred protecting group for positions 3 and 4 of the galactosyl moiety is isopropylidene.

The following examples are intended to illustrate but not to limit the invention.

EXAMPLE 1

Preparation of 2-(Trimethylsilyl) ethyl 2,6-di-O-benzoyl-4-O-(2,6-di-O-benzoyl -3,4-O-isopropylidene-β-D-galactopyranosyl)-β-glucopyranoside (7a)

2-(Trimethylsilyl) ethyl 4-O-(3,4-O-isopropylidene-β-D-galactopyranosyl) -β-D-glucopyranoside (K. Jansson et al., J. Org. Chem. (1988) 53: 5629–5647; 6.6 g, 13.75 mmol) was dissolved in dry pyridine (120 mL). The mixture was cooled to –45° C. and stirred, while benzoyl chloride (9.07 mL, 77.4 mMol.) was added dropwise, and stirring was continued for 4 h at –45° C.

T.l.c. (8.5:1.5 toluene-ethyl acetate) revealed the presence of a major product, faster-migrating than the starting acetal. A small proportion of a still faster-migrating product (pentabenzoate) was also revealed by t.l.c. The mixture was poured into ice-water and extracted with dichloromethane. The dichloromethane solution was successively washed with water, aqueous $NaHCO_3$, and water, dried ($Na_2SO_4$), and concentrated. The concentrate was applied to a column of silica gel with 9:1 toluene-ethyl acetate as the eluent and gave a solid which crystallized from methanol to afford 7a (5.2 g, 42.3%), $[\alpha]_D$ +17.5 (C, 1.1, chloroform). $^{13}C$ NMR ($CDCl_3$): δ167.16, 166.13, 165.87, 165.83 (4×PhCO), 111.23 ($C(CH_3)_2$), 101.50, 100.24 (C-1, C-1'), 82.57, 77.02 (C-3', C-4), 73.65, 73.44, 73.01, 72.96, 72.06, 71.97 (C-5, C-5', C-4', C-3, C-2, C-2'), 67.21 ($OCH_2CH_2Si$), 63.69, 62.72 (C-6, C-6'), 27.62, 26.28 [$C(CH_3)_2$], and 17.75 ($CH_2CH_2Si$).

EXAMPLE 2

Preparation of Benzyl 2,6-di-O-benzoyl-4-O-(2,6-di-O-benzoyl-3,4-O -isopropylidene-β-D-galactopyranosyl)-β-D-glucopyranoside (7b)

A stirred and cooled (–45° C., bath) solution of benzyl 4-O-(3,4-O -isopropylidene-β-D-galactopyranosyl)-β-D-glucopyranoside (5 g, 10.6 mmol; D. Beith-Halahmi et al., Carbohydr Res. (1967) 5: 25) in dry pyridine (120 mL), was treated with benzoyl chloride (6 mL, 51.8 mmol), dropwise, and the stirring was continued for 4 h at –45° C. T.l.c. (8.5:1.5 toluene- ethyl acetate) revealed the presence of a major product, faster-migrating than the starting acetal. A small proportion of a still faster-migrating product (pentabenzoate) was also revealed by t.l.c. The mixture was poured into ice-water and extracted with dichloromethane. The dichloromethane solution was successively washed with water, aqueous $NaHCO_3$, and water, dried ($Na_2SO_4$), and concentrated. The concentrate was then applied to a column of silica gel and eluted with 9:1 toluene-ethyl acetate. On concentration, the fractions corresponding to the major product gave a solid residue which crystallized from hot methanol to afford 7b (5.53 g, 59%); m.p. 159–161° C.; $[\alpha]_D$ –4.2° (c, 1.3, chloroform). $^1H$ NMR ($CDCl_3$): δ8.2–7.00 (m, 25H, arom.), 5.36 (t, 1H, J 7.8 Hz, H-2'), 5.30 (dd, 1 H, J 8.0, and 9.5 Hz, H-2), 4.68 (d, 1H, J 8.0 Hz, H-1'), 4.56 (d, 1H, J 8.1 Hz, H-1), 3.94 (dd, 1 H, J 8.2 and 9.6 Hz, H-3), 3.75 (dd, 1 H, J 8.2 and 9.7 Hz, H-4), and 1.65 and 1.35 [2s, 3H each, $C(CH_3)_2$]; $^{13}C$ NMR ($CDCl_3$): δ167.16, 166.17, 165.90, and 165.86 (4×PHCO),111.86 ($C(CH_3)_2$), 102.10, 99.49 (C-1, C-1'), 82.99(C-4), 77.60 (C-3'), 74.02 (C-4'), 73.60, 73.50, 72.66 (C-2, C-2', C-3, C-5, C-5'), 70.73 ($PhCH_2$), 64.29 and 63.20 (C-6, C-6'), and 28.26 and 26.88 [$(CH_3)_2C$]; positive ion LSIMS: 889.7 (M+H)+, 781.6 M-OBn)+-, negative ion LSIMS: 934.1 ($M+NO_2$)–, 1041.1 (M+mNBA)–.

EXAMPLE 3

Preparation of Benzyl 2,6-di-O-benzoyl-3-O-(2,3,4-tri-O-benzyl-α-L -fucopyranosyl)-4-O-(2,6-di-O-benzoyl-3,4-O-isopropylidene-β-D -galactopyranosyl)-β-D-glucopyranoside (9b)

A mixture of compound 7b (4 g, 4.5 mmol), methyl 2,3,4-tri-O-benzyl-1-thio-α-L-fucopyranoside 8 (3.6 g, 7.75 mmol) and powdered 4 A molecular sieves (10 g) in 5:1 dichloroethane-N,N-dimethylformamide (120 mL), protected from moisture, was stirred for 2h at room temperature. Cupric bromide (2 g, 9 mmol) and tetrabutylammonium bromide (0.29 g,0.9 mmol) were added and the stirring was continued for 35 h at room temperature. More of the donor 8 (1.2 g, 2.6 mmol, in 14.4 mL of 5:1 dichloroethane-N,N-dimethylformamide), cupric bromide (0.67 g, 0.3 mmol), and molecular sieves 4 A (2 g) were added, and the stirring was continued for 16 h at room temperature. T.l.c. (9:1 toluene-ethyl acetate) then showed the presence of a major product, faster-migrating than 7b; a trace of unchanged 7b was also revealed by t.l.c. The mixture was filtered (a bed of Celite) and the solids thoroughly washed with chloroform. The filtrate and washings were combined and washed with aqueous $NaHCO_3$ and water, dried and concentrated. The residue was applied to a column of silica gel and eluted with 9.5:0.5 toluene-ethyl acetate. Concentration of the fractions corresponding to the major product furnished a solid, which crystallized from ether to afford 9b (3.68 g, 76%), based on reacted 7b. Compound 9b had m.p. 180°–181° C.; $[\alpha]_D$—8° (c, 1.1, chloroform). $^1H$ NMR $(CDCl_3)$: δ5.48 (dd,1 H, J 9.3 and 7.9 Hz, H-2'), 5.40 (d, 1 H, J 3.8 Hz, H-1 fuc), 5.22 (dd, 1 H, J 8.6 and 7.3 Hz, H-2), 4.49 (d, 1 H, J 8.6 Hz, H-1 ), 4.42 (d, 1 H, J 7.9 Hz, H-1'), 3.90 (dd, 1 H, J 10.2 and 3.8 Hz, H-2 fuc), 1.49 and 1.35, (s, 1 H each, $C(CH_3)_2$), and 1.29 (d, 3 H, J 6.6 Hz, H-6 fuc); $^{13}C$, $(CDCl_3)$: δ166.86–165.22 (4×PhCO), 111.44 $[C(CH_3)_2]$, 100.84, 99.80 (C-1,C-1'), 63.17, 63.01 (C-6C-6'), 28.35, 26.86 $[C(CH_3)_2]$, and 17.48 (C-6''); positive ion LSIMS: 1197.9 (M-OBn)+, negative ion LSIMS: 1350.2 $(M+NO_2)$—, 1 457.3 (M+mNBA)—.

EXAMPLE 4

Preparation of 2-(Trimethylsilyl) ethyl 2,6-di-O-benzoyl-3-O-(2,3,4-tri-O-benzyl -α-L-fucopyranosyl)-4-O-(2,6-di-O-benzoyl-3,4-O-isopropylidene-β-D -galactopyranosyl)-β-D-glucopyraoside (9a)

A mixture of compound 7a (5.2 g, 5.78 mmol), compound 8 (4.68 g,10.17 mmol) and powdered 4A molecular sieves (6 g), in 5:1 dichloroethane-N,N-dimethylformamide (135 mL), protected from moisture, was stirred for 2 h at room temperature. Cupric bromide (2.6 g, 11.7 mmol), and tetrabutylammonium bromide (3.77 g, 11.7 mmol) were added, and the stirring was continued for a total of 48 h at room temperature, additional amounts of 8 (2.34 g, 5.09 mmol, in 60 mL of 5:1 dichloroethane-N,N-dimethylformamide), cupric bromide (1.3 g, 5.85 mmol), tetrabutylammonium bromide (1.9 g, 5.85 mmol) and 4A molecular sieves (3 g) being added after 24 h. T.l.c. (9:1 toluene- ethyl acetate) revealed the presence of a major product, faster-migrating than 7a, Some unreacted 7a was also revealed by t.l.c. After processing as described for 7b (to give 9b), followed by column chromatography, compound 9a (6.7 g, 88%) was obtained as an amorphous solid; positive ion LSIMS: 1442.6 (M+Na)+, 1340.8 $(MN–NaSO_3)$+, negative LSIMS: 1396.2 (M-Na)—,

EXAMPLE 5

Preparation of Benzyl 2,6-di-O-benzoyl-3-O-(2,3,4-tri-O-benzyl-α-L -fucopyranosyl)-4-O-(2,6-di-O-benzoyl-β-D-galactopyranosyl)-β-D-glucopyranoside (10b)

Compound 9b (1.0 g) in 70% aqueous acetic acid (600 mL), was stirred at 85°–90° C., the progress of the reaction being monitored by t.l.c.(4:1 toluene ethyl acetate). After 2.5 h, most of the starting acetal 9b was converted into a slower-migrating product. T.l.c. also indicated some cleavage of the α-L-fucosyl linkage, as evidenced by the presence of two by-products, one of which was marginally faster-migrating than the product (tribenzyl fucose), and the other slower-migrating (disaccharide product). The acetic acid was evaporated under diminished pressure (~40° C.), the last traces being removed by co-evaporation with several added portions of toluene. The residue so obtained was purified in a column of silica gel with 9:1 toluene-ethyl acetate as the eluent to give 10b (0.6 g, 61.8%), as an amorphous solid. $^{13}C$ NMR $(CDCl_3)$: δ167.25, 166.80, 165.23 (4×PhCO), 100.65, 99.85 (C-1, C-1'), 98.18 (C-1 fuc),79.55, 79.08 (C-3, C-4), 75.77, 73.20, 72.97, 70.30 (4×PhCH2), 63.38, 62.33 (C-6, C-6'), and 17.16 (C-6 fuc); positive ion LSIMS: 1263.7 (M+H–2H)+, 1157.7 (M-OBn)+, negative ion LSIMS: 1417.1 (M+mNBA)–, 1310.3 $(M+NO_2)$–, 1263.2 (M-H)–.

EXAMPLE 6

Preparation of 2-(Trimethylsilyl) ethyl 2,6-di-O-benzoyl-3-O-(2,3,4-tri-O-benzyl -α-L-fucopyranosyl)-4-O-(2,6-di-O-benzoyl-β-D-galactopyranosyl)-β-D-glucopyranoside (10a)

Compound 9a (3 g, 2.3 mmol) was taken in 70% aqueous acetic acid (300 mL) and the mixture was heated, with stirring, for 2 h at 85°–90° C. (bath). T.l.c. (4:1 toluene-ethyl acetate) showed the presence of a major product with chromatographic mobility comparable to that of 10b. Processing as described for 9b (to give 10b), followed by column chromatography, gave trisaccharide diol 10a (2.3 g, 79%) as an amorphous solid; –20.6° (c, 1.1, chloroform). $^{13}C$ NMR $(CDCl_3)$: δ167.26, 166.98, 166.78, 165.04 (4×PhCO), 101.31,100.55 (C-1, C-1'), 98.19 (C-1 fuc), 79.56, 78.98 (C-3, C-4), 75.75, 73.19, 72.98 (3×$PhCH_2$), 67.84 ($OCH_2CH_2Si$), 63.48, 62.19 (C-6, C-6'), 18.45 ($OCH_2CH_2Si$), and 17.16 (C-6 fuc).

EXAMPLE 7

Preparation of Benzyl 2.6-di-O-benzoyl-4-O-(4-O-acetyl-2, 6-di-O-benzoyl-β-D -galactopyranosyl)-3-O-(2,3,4-tri-O-benzyl-α-L-fucopyranosyl)-β-D-glucopyranoside (11b)

Compound 10b (0.56 g) was dissolved in a mixture of benzene (30 mL) and triethylorthoacetate (30 mL), containing 4-toluenesulfonic acid (0.15 g), and the mixture stirred for 1 h at room temperature. The acid was neutralized with a little triethylamine, and the mixture evaporated to dryness. It was then taken in 80% aqueous acetic acid (50 mL) and stirred for 40 min at room temperature. T.l.c. (4:1 toluene-ethyl acetate) showed the presence of a major product,faster-migrating than diol 10b. The acetic acid was removed under diminished pressure, and several portion of toluene were added to, and evaporated from the residue to furnish 11b (0.56 g, 96.6%) as an amorphous solid, $[\alpha]_D$–14.3° (c,1.1, chloroform). $^1H$ NMR $(CDCl_3)$: δ8.20–7.00 (m, 40 H, arom.), 5.51 (t, 1 H, J 8.0 Hz, H-2'), 5.38 (d, 1 H, J 3.8 Hz, H-1 fuc), 5.30 (d, 1 H, J 3.8 Hz, H-4'), 5.20 (dd, 1 H, J 8.1 and 10.0 Hz, H-2), 4.62 (d, 1 H, J 8.2 Hz, H-1), 4.44 (d, 1 H, J 7.9 Hz, H-1'), 1.82 (s, 3 H, $CH_3CO$), and 1.34 (d, 3 H, J 6.4 Hz, H-6 fuc). $^{13}C$ NMR $(CDCl_3)$: δ170.38 ($CH_3CO$), 166.15, 165.72, 165.57, 164.56 (4×PhCO), 100.45, 99.23 (C-1, C-1'), 97.54 C-1 fuc), 79.48 (C-3), 77.57 (C-4), 74.08, 72.94, 72.70, 70.15 (4×PhCH2), 62.54, 60.78 (C-6, C-6'), 20.59 ($CH_3CO$), and 16.88 (C-6 fuc); positive ion LSIMS: 1307.1 (M+H)+), 1200.8 (M-OBn)+, negative ion LSIMS: 1460.9 (M+mNBA)–, 1353.6 $(M+NO_2)$–, 1306.8 (M-H)–.

EXAMPLE 8

Preparation of 2-(Trimethylsilyl) ethyl 2.6-di-O-benzoyl-4-O-(4-O-acetyl-2.6-di -O-benzoyl-β-D-galactopyranosyl)-3-O-(2,3,4-tri-O-benzyl -α-L-fucopyranosyl)-β-D-galactopyranoside (11a)

A solution of compound 10A (1.87 g), in a mixture of benzene (50 mL) and triethyl orthoacetate (50 mL), containing 4-toluenesulfonic acid (0.25 g) was stirred for 1 h at room temperature. The acid was then neutralized with a few drops of triethylamine, and the mixture evaporated to dryness. The residue was mixed with 80% aqueous acetic acid (100 mL) and the mixture stirred for 40 min at room temperature. Processing as described for 10b (to give 11b), gave the title compound 11a (1.86 g,89%); a white amorphous solid; $[\alpha]_D$ −2.7° (c, 1.1, chloroform). $^{13}$C NMR (CDCl$_3$): δ171.03 (CH3CO), 166.78, 166.35, 166.18, 165.02 (4×PhCO), 101.27, 101.09 (C-1, C-1'), 98.17 (C-1 fuc), 80.10, 78.20 (C-3, C-4), 74.67, 73.54, 73.30 (3×PhCH$_2$), 67.86 (OCH$_2$CH$_2$Si), 63.31, 61.42 (C-6, C-6'), 21.21 (CH$_3$CO), 18.47 (OCH$_2$CH$_2$Si), and 17.53 (C-6 fuc); negative ion LSIMS: 1470.8 (M+mNBA)−, 1363.7 (M+NO2)−.

EXAMPLE 9

Preparation of Benzyl 2,6-di-O-benzoyl-3-O-(2,3,4-tri-O-benzyl-α-L -fucopyranosyl)-4-O-(sodium 4-O-acetyl-2,6-di-O-benzoyl-β-D -galactopyranosyl 3-sulfate)-β-D-glucopyranoside (12b)

A mixture of compound 11b (0.6 g, 0.46 mmol) and sulfur trioxide-pyridine complex (0.6 g, 6.3 mmol) in dry pyridine (50 mL) was stirred for 2 h at 55°–60° C. (bath), and then for 16 h at room temperature. T.l.c. (6:1 chloroform-methanol) showed the disappearance of 11b and the presence of a single slower-migrating product. Methanol (5 mL) was added, and the mixture stirred for 15 min (to decompose excess reagent). It was then concentrated and purified in a column of silica gel by elution with 10:1, followed by 6:1 chloroform-methanol. Upon concentration, the fractions corresponding to the product gave a solid residue, which was dissolved in 1:1 chloroform-methanol (30 mL) and treated with Amberlite IR 120 (Na+) cation-exchange resin, and the mixture stirred for 1 h at room temperature. It was then filtered and evaporated to dryness to give 12b (0.58 g, 89%) as an amorphous solid; $[\alpha]_D$ −5.1° (c, 1.8, 1:1 chloroform-methanol); positive LSIMS: 1433 (M+Na)+, 1411.1 (M+H)+, negative LSIMS: 1563.9 (M+mNBA)−, 1386.7 (M-Na)−.

EXAMPLE 10

Preparation of 2-(Trimethylsilyl) ethyl 2,6-di-O-benzoyl-3-O-(2,3,4-tri-O-benzyl -α-L-fucopyranosyl)-4-O-(sodium 4-O-acetyl-2,6-di-O-benzoyl-α-D -galactopyranosyl 3-sulfate)-β-D-glucopyranoside (12a)

A mixture of compound 118, (0.45 g, 0.39 mmol) and sulfur trioxide-pyridine complex (0.45 g, 4.7 mmol) in dry pyridine (25 mL) was stirred for 2 h at 55°–60° C., and then overnight at room temperature. After processing and purification, in a manner similar to the afore described, compound 12a (0.46 g, 95.8% ) was obtained as an amorphous solid; $[\alpha]_D$ +2.2° (c, 1.5, 1:1 chloroform-methanol); positive ion LSIMS: 1442.6 (M+Na)+, 1341.1 (M-NaSO$_3$)−, negative ion LSIMS: 1395.5 (M-Na)−.

EXAMPLE 11

Preparation of O-αL-fucopyranosyl-(1→3)-O-[sodium β-D-galactopyranosyl 3-sulfate-(1→4)]-D-glucopyranose (13b).

Compound 12b (0.58 g) in methanol (50 mL), containing a catalytic amount of sodium methoxide, was stirred overnight at 45°–50° C. T.l.c. (13:6:1 chloroform-methanol-water) showed the presence of a single slower-migrating product. After cooling to room temperature, Amberlite IR 120 (H+) cation-exchange resin was added till the mixture became neutral (pH paper). It was then filtered directly into a flask containing Amberlite IR 120 (Na+) cation-exchange resin, and the mixture stirred for 45 min. It was then concentrated, and the residue repeatedly extracted with hexane-ether mixture to remove methyl benzoate. The partially-protected intermediate so obtained (0.38 g,) was sufficiently pure to be utilized directly in the next step; negative ion LSIMS: 928.1 (M-Na)−. A portion (0.35 g), without further purification, was taken in 80% aqueous methanol (30 mL), containing 10% palladium-on-carbon (0.35 g). The mixture was stirred overnight at room temperature under a slight overpressure of H$_2$, when t.l.c. (5:4:1, or 13:6:1 chloroform-methanol-water) indicated the presence of a slower-migrating product, together with traces of some faster-migrating contaminants (presumably due to incomplete hydrogenolysis). The mixture was filtered (Celite bed) directly onto Amberlite IR 120 (Na+) cation-exchange resin, and the solids thoroughly washed with aqueous methanol. After stirring with the resin for 1 h, the mixture was filtered and concentrated to a small volume, which was applied to a column of silica gel and eluted with 5:4:1 chloroform-methanol-water. Fractions corresponding to the product were pooled, concentrated to a small volume and treated with Amberlite IR 120 (Na+) cation-exchange resin. The resin was filtered off and washed with water, and the filtrate and washings combined, refiltered (0.2 μM Cellulose acetate syringe filter), and lyophilized to give 13b, (183 mg, 84.3%; $[\alpha]_D$ −20.5° (c, 0.6, water). 1 H NMR (D$_2$O): δ5.45 [d, 1 H, J 4.13 Hz, H-1 fuc (β)], 5.39 [d, 1 H, J 3.81 Hz, H-1 fuc (α)], 5.18 (d, 1 H, J 3.81 Hz, H-1), 4.66 (d, 1 H, J 7.93 Hz, H-1'), 4.55 [d, 1 H, J 7.62 Hz, H-1 (β)]; negative ion LSIMS: 567.5 (M-Na)−, 421 (M-Na-Fuc)−.

EXAMPLE 12

Preparation of 2-(Trimethylsilyl)ethyl O-α-L-fucopyranosyl-(1→3)-O-[sodium -β-D-galactopyranosyl 3-sulfate-(1→4)]-β-D-glucopyranoside (13a)

Compound 12a (0.45 g) was O-deacylated in methanolic sodium methoxide (50 mL), exactly as described for 10, to afford the corresponding partially benzylated intermediate (0.29 g), which showed positive ion LSIMS: 983.9 (M+Na)+, 882.1 (M-NaSO$_3$), negative ion LSIMS: 938.0(M-Na)−. This compound (0.24 g) without any further purification, was subjected to catalytic hydrogenolysis in 80% aqueous methanol (30 mL) in the presence of 10% palladium-on-carbon (0.24 g), and then processed in a manner analogous to the afore described to afford compound 13a (125 mg, 72.7%), as a white fluffy material; $[\alpha]_D$ −49.2° (c, 0.6. water) $^1$H NMR (D$_2$O): δ5.45 (d, 1 H, J 4.22 Hz, H-1 fuc), 4.55 (d,1 H, J 8.06 Hz, H-1'),4.49 (d, 1 H, J 8,44 Hz, H-1), 4.32 (dd, 1 H, J 3.45 and 9.98 Hz, H-3'); positive ion LSIMS: 713.8 (M+Na)+, negative ion LSIMS: 667.6 (M-Na)−.

EXAMPLE 13

Preparation of a Multivalent Ligand, N.6N,6N' Tris (20) Lys-Tyr-Lys

Compound 13a or 13b, prepared in Example 12, may be derivatized to the peptide Lys-Tyr-Lys to obtain the trivalent conjugate derivatized at the two ε-amino lysine groups and the α-amino N-terminal of the peptide. To obtain this trivalent compound, 50 μl of 2 mM peptide Lys-Tyr-Lys (100 nmol) in 100 mM sodium carbonate, pH 9, are placed in a small Eppendorf tube containing 5 μl of 200 mM 20 (1 mmol), and the sample is evaporated to dryness in a Speed-Vac for about 30 minutes.

After evaporation, 50 μl of 800 mM NaCN·BH$_3$ (recrystallized, 40 μmol) in 100 mM sodium carbonate, pH 9, is added and the mixture is incubated for 48 hours at 55° C. The resulting incubated mixture is run on a GPC peptide HPLC sizing column and fractions are collected and assayed for protein content by BCA protein assay. Protein-containing fractions are pooled, lyophilized and submitted for mass spectroscopy.

The results would show the formation of the derivatized peptide as containing 1, 2 or 3 moieties of compound 13a or 13b.

The trivalent derivative would be especially effective in inhibiting the binding of lactose to hepatocytes in an assay conducted as described by Lee, R. et al., Biochem (1984) 23:4255.

EXAMPLE 14

Preparation of Octyl 4-O-(2,3,4,6-tetra-O-acetyl-β-D -galactopyranosyl)-2,3,6-tri-O-acetyl-O-Dglucopyranoside (17)

A mixture of n-octanol (20 mL), silver oxide (10 g), and dririte (25 g) in 1:1 benzene-ether (250 mL) was stirred at room temperature, under anhydrous conditions, for 1 h. Acetobromolactose (16, 25 g, 35.7 mmol) was added and the mixture was stirred overnight at room temperature. The solids were then filtered off over a celite bed and washed with chloroform. The filtrate was concentrated, hexane (4×50 ml) was added to the product and decanted from the residue and the crude product was purified on a silica gel column (3:1 followed by 2:1 hexane-ethyl acetate) to yield 17 (15.8 g, 59%), as an amorphous white solid. An analytical sample was crystallized from dichloromethane-ether-heptane; m.p. 83°–85° C.; [α]$_D$ –14.7° (c 1.1 chloroform), t.l.c. (1:1 ethyl acetate-hexane). $^{13}$C NMR (CDCl$_3$): δ170.41–169.10 (CH$_3$CO), 101.05, 100.58 (C-1, C-1'), 76.34 (C-4), 70.21 [OCH$_2$(CH$_2$)$_6$], 62.10, 60.85 (C-6, C-6'), 31.79–22.64 [(CH$_2$)$_6$CH$_3$], 14.09 (CH$_3$); negative LSIMS: 901.8 (M-H+mNBA)–, 747.8 (M-H)–, 705.7,663.7, 621.7 (M-Ac, 2Ac, 3Ac, respectively); positive LSIMS: 771.9 (M+Na)+.

EXAMPLE 15

Preparation of Octyl 4-O-β-D-galacopyranosyl-β-D-glucopyranoside (18)

Compound 17 (30 g) was dissolved in dry methanol (150 mL), containing a catalytic amount of sodium methoxide, and the mixture was stirred at room temperature. In about 30 minutes, crystallization of the deacetylated material ensued, and the mixture was stirred overnight at room temperature. The base was neutralized with glacial acetic acid, and the crystalline material was filtered and washed with a mixture of methanol-ethanol and dried in air and then in vacuo to yield 18, (15.2 g, 83.5%); m.p. 179°–181° C; [α]$_D$ –10.9° (c 1.0, methanol), t.l.c. (13:6:1 chloroform-methanol-water or 3:2:1 ethyl acetate-propanol-water). $^{13}$C NMR (DMSO-d$_6$): δ104.20, 102.89 (C-1, C-1'), 81.15 (C-4), 69.10 [OCH$_2$(CH$_2$)$_6$], 60.88, 60.77 (C-6, C-6'), 31.64–22.48 [(CH$_2$)$_6$CH$_3$], and 14.34 (CH$_3$); negative LSIMS: 453.4 (M-H)–. An additional amount of 18 (1.6 g) was obtained after deionization and concentration of the mother liquor (total yield 92%).

EXAMPLE 16

Preparation of Octyl 4-O-(3,4-O-isopropylidene-β-D -galactopyranosyl)-β-D-glucopyranoside (19)

Method (a): A Mixture of 18 (5 g) and camphorsulfonic acid (0.2 g) in 2,2-dimethoxypropane (200 mL) was stirred for 48 h at room temperature. The acid was neutralized with triethylamine and the mixture concentrated. The residue was mixed with toluene and evaporated to remove traces of triethylamine. The residue was taken in 10:1 methanol-water (200 mL) and boiled overnight. The mixture was concentrated, and the residue co-evaporated with ethanol. Crystallization from acetone-heptane yielded compound 19 (3.6 g, 66.2%); m.p. 145°–147° C.; +6.4° (c 1.25, chloroform), t.l.c. (9:1 chloroform-methanol). $^{13}$C NMR (CD$_3$OD): δ111.67 [C(CH$_3$)$_2$], 104.73 (C-1, C-1'), 81.57, 81.41 (C-3', C-4) 76.90, 75.91, 75.63, 75.40, 75.02 (C-2, C-2', C-4', C-5, C-5'), 71.54 [OCH$_2$(CH$_2$)$_6$–), 62.98, 62.43 (C-6, C-6'), 29.04, 27.14 [(CH$_3$)$_2$C], 31.66–24.31 [CH$_2$(CH$_2$)$_6$], and 15.07 (CH$_3$); negative LSIMS: 493.5 (M-H)–, positive LSIMS: 517.6 (M+Na)+.

Method (b): A mixture of 18 (5 g) and 4-toluenesulfonic acid (1 g), in acetone (500 mL) was boiled for about 4 h. The acid was neutralized by the addition of triethylamine, and the mixture concentrated. Addition of acetone-heptane caused the crystalliza-tion of 19 (4 g, 73.5%).

EXAMPLE 17

Preparation of Octyl 2.6-di-O-benzoyl-4-O(2,6-di-O-benzoyl-3,4-O -isopropylidene-β-galactopyranosyl)-β-D-glucopyranoside (20)

A solution of benzoyl chloride (8.1 mL, 67.5 mmol) in pyridine (35 mL) was added dropwise to a solution of 19 (7.5 g, 15.2 mmol) in pyridine (140 mL) at –450° C. and the mixture was stirred for 3–4 h at –40°–45° C. The mixture was poured into ice-water and extracted with dichloromethane (3×50 ml). The dichloromethane solution was successively washed with water, ice-cold 5% aqueous H$_2$SO$_4$, aqueous NaHCO$_3$, water, dried (Na$_2$SO$_4$), and concentrated. The crude product was crystallized from methanol-2-propanol (3:1 v/v) to give the desired tetrabenzoate 20, (8.2 g, 59.4%). An analytical sample was obtained by recrystallization from dichloromethane- methanol, m.p. 133°–134.5° C; [α]$_D$+16.9° (c 0.9, chloroform), t.l.c. (8.5:1.5 toluene-ethyl acetate). $^1$H NMR (CDCl$_3$): δ8.20–7.10 (m, 20 H, arom.), 5.37 (t, 1 H, J 7.8 Hz, H-2'), 5.22 (dd, 1 H, J 8.2 and 9.5 Hz, H-2, 4.67 (d, 1 H, J 8.2 Hz, H-1'), 4.53 (d, 1 H, J 8.1 Hz, H-1), and 1.65 and 1.35 [2s, 3 H, each, C(CH$_3$)$_2$]; $^{13}$C NMR (CDCl$_3$): δ166.55–165.27 (4×PhCO), 111.24 [C(CH$_3$)$_2$], 101.51, 100.95 (C-1, C-1'), 82.48 (C-4), 77.03 (C-3'), 73.45 (C-4'), 73.02, 72.89, 72.07 and 72.02 (C-2, C-2', –3, C-5, C-5'), 70.02 [CH$_2$(CH$_2$)$_6$, 63.69, 62.70 (C-6, C-6'), 31.64, 29.33, 29.14, 29.05, 25.71, and 22.55 [(CH$_2$)$_6$CH$_3$], 27.62, 26.27 [(CH$_3$)$_2$C], and 14.03 (CH3); negative LSIMS: 1063.2 (M-H+mNBA)–, 956.2 (M+NO$_2$)–.

EXAMPLE 18

Preparation of Octyl 2,6,di-O-benzoyl-3-O-(2,3,4-tri-O-benzyl-α-L -fucopyranosyl)-4-O-(2,6-di-O-benzoyl-3,4-O-isopropylidene -β-D-galactopyranosyl)-β-D-glucopyranoside (21)

A mixture of compound 20 (7 g, 7.7 mmol), methyl 2,3,4-tri-O-benzyl-1-thio-L-fucopyranoside (8, 6.5 g, 14.1 mmol) and powdered 4 A molecular sieves (10 g), in 5:1 dichloroethane-N,N-dimethyl-formamide (150 mL), protected from moisture, was stirred for 2 h at room temperature. Cupric bromide (4 g, 18 mmol) and tetrabutyl-ammonium bromide (2 g, 6.2 mmol) were added and the mixture was stirred overnight at room temperature. More of the donor 8 (2 g, 4.3 mmol, in 12 mL of 5:1 dichloroethane-N,N-dimethylformamide) and cupric bromide (1.2 g, 2.6 mmol) were added, and the stirring was continued for 16 h at room temperature. The mixture was filtered over celite and the solids were thoroughly washed with dichloromethane. The flitrate and washings were combined and stirred for 15 min with 10% Na EDTA solution. The organic solution was separated, and this process was repeated (2 ×10% Na EDTA followed by 2×5% Na EDTA solution). The organic phase was washed with water, dried ($Na_2SO_4$), and concentrated to a thick syrup under diminished pressure. The residue was crystallized from ether-heptane to yield 21, (8.5 g, 83%). An analytically pure sample of 21 was obtained by crystallization from dichloromethane-ether, m.p. 152°–153° C.; $[\alpha]_D$+2.5° (c 1.1, chloroform), t.l.c. (8.5:1.5 toluene-ethyl acetate). $^{13}C$ NMR ($CDCl_3$): δ166.24, 166.05, 164.71, 164.52 (4×PhCO), 110.83 [$C(CH_3)_2$], 101.43, 100.24 (C-1, C-1'), 97.38 (C-1 fuc), 74.89, 72.63, 72.43 (3×$CH_2Ph$), 70.11 [$OCH_2(CH_2)_6$–], 62.58, 62.48 (C-6, C-6'), 31.67–22.56 [$(CH_2)_6CH_3$], 27.75, 26.25 [$(CH_3)_2C$], 16.90 (C-6 fuc), and 14.05 ($CH_3$); negative LSIMS: 1480.1 (M-H+mNBA)–, positive LSIMS: 1349.9 (M+Na)+.

EXAMPLE 19

Preparation of Octyl 2.6-di-O-benzoyl-3-O-(2,3,4-tri-O-benzyl-α-L-fucopyranosyl)-4-O-(2,6-di-O-benzoyl-β-D-galactopyranosyl)-β-D-glucopyranoside (22)

A solution of 21 (8 g) in chloroform (300 mL), containing trifluoroacetic acid (18 mL) and water (3–4 mL) was stirred vigorously for 10 h at room temperature, the reaction being monitored by t.l.c. (19:1 or 9:1 chloroform-acetone), which indicated the progressive diminishing of 21 with a simultaneous increase in the slower-migrating diol 22. Some removal of the fucopyranosyl residue also occurred as evidenced by the presence in t.l.c. of a spot migrating marginally faster than 22 (chromato-graphic mobility identical to that of tribenzyl fucose), and a slower migrating product (presumably the lactoside triol). T.l.c. also revealed the presence of a small proportion of unchanged 21, but the reaction was terminated to avoid excessive defucosylation. The mixture was poured into ice-cold, saturated aqueous $NaHCO_3$ solution and stirred for 15 min. The chloroform solution was separated and washed again with $NaHCO_3$ solution, followed by water, dried ($Na_2SO_4$), and concentrated. The residue was purified using a silica gel column (5–20% ethyl acetate in toluene) to yield unreacted 21 (0,8 g), tribenzyl fucose, and 22 (5.4 g, 69.6%) as a foam; $[\alpha]_D$–20.20° (c 1.1, chloroform). $^{13}C$ NMR ($CDCl_3$): δ167.22–165.11 (4×PhCO), 102.09, 100.60 (C-1, C-1'), 98.20 (C-1 fuc), 79.56, 79.07 (C-3, C-4), 75.77, 73.16, 72.98 (3×$CH_2Ph$), 70.65 [$OCH_2(CH_2)_6$], 68.41, 67.12 (C-6, C-6'), 32.27 –23.16 ([$OCH_2(CH_2)_6$], 17.17 (C-6 fuc), and 14.65 ($CH_3$).

EXAMPLE 20

Preparation of Octyl 2,6-di-O-benzoyl-4-O-(4-O-acetyl-2,6-di-O-benzoyl-β-D-galacto-pyranosyl)-3-O-(2,3,4-tri-O-benzyl-α-L -fucopyranosyl)-β-D-glucopyranoside (23)

Compound 22 (5 g) was dissolved a 1:1 mixture of benzene and triethylorthoacetate (110 mL), containing 4-toluenesulfonic acid (0.2 g), and the mixture was stirred for 1 h at room temperature. The acid was neutralized with triethylamine, and the mixture evaporated to dryness. The residue was dissolved in 80% aqueous acetic acid (75 mL) and stirred for 40 min at room temperature. The acetic acid was evaporated under diminished pressure and the last traces were removed by co-evaporation with toluene to yield 23 (4.7 g, 91.3%); $[\alpha]_D$, –4.5° (c 0.8, chloroform), t.l.c. (5:1 ethyl acetate-toluene). $^{13}C$ NMR ($CDCl_3$): δ170.98 ($COCH_3$), 166.75, 166.33, 166.18, 165.07 (4×PhCO), 102.03, 101.08 (C-1, C-1'), 98.16 (C-1 fuc), 80.07, 78.23 (C-3, C-4), 74.69, 73.53, 73.24 (3×$PhCH_2$), 70.66 [$OCH_2(CH_2)_6$], 63.23, 61.42 (C-6, C-6'), 32.25–23.14 [$(CH_2)_6CH_3$], 21.20 ($COCH_3$), 17.49 (C-6 fuc), and 14.63 ($CH_3$).

EXAMPLE 21

Preparation Of Octyl 2,6-di-O-benzoyl-3-O-(2,3,4-tri-O-benzyl-α-L-fucopyranosyl)-4-O-(sodium 4-O-acetyl-2,6-di-O -benzoyl-β-D-galactopyranosyl 3-sulfate)-β-glucopyranoside (24)

A mixture of 23 (4.5 g) and sulfur trioxide-pyridine complex (4.5 g) in dry pyridine (65 mL) was stirred for approximately 40 min at 55°–60° C. After cooling to room temperature, methanol (5 mL) was added and the mixture stirred for 20 min, concentrated and the residue co-evaporated with toluene. The residue was purified on a silica gel column (19:1 followed 9:1 chloroform-methanol). On evaporation of the fractions corresponding to the product, the residue so obtained was dissolved in 1:1 chloroform-methanol and stirred with Amberlite IR 120 (Na+) cation-exchange resin for 1 h at room temperature. The resin was filtered off and washed with chloroform-methanol and the solution was evaporated to yield 24 (3.2 g, 84.7%) as an amorphous solid; $[\alpha]_D$+5.3° (c 1.1, chloroform-methanol 1:1 v/v), t.l.c. (9:1 chloroform-methanol).

EXAMPLE 22

Preparation Of Octyl O-α-L-fucopyranosyl-(1→3-O-[sodium β-D-galactopyranosyl 3-sulfate-(1→4)]-β-D-glucopyranoside (26)

Compound 24 (4.4 g) in methanol (100 mL), containing a catalytic amount of sodium methoxide, was stirred overnight at 45°–500° C. (t.l.c. 6:2:1 ethyl acetate-2-propanol-water). The mixture was cooled to room temperature, neutralized (pH paper) with Amberlite IR 120 (H+) cation-exchange resin, filtered directly into a flask containing Amberlite IR 120 (Na+) cation-exchange resin, and stirred for 45 rain at room temperature. The resin was filtered and washed with methanol, the flitrate and washings combined and concentrated. Several portions of hexane were added to, and decanted from the residue to yield the partially protected intermediate 25 (2.7 g, 90%); $[\alpha]_D$, –54.1° (c 0.8, methanol), t.l.c. (6:2:1 ethyl acetate-2-propanol-water); positive LSMIS: 995.6 (M+Na)+, negative LSIMS: 949.7 (M-Na).

A solution of 25 (2.6 g) in 4:1 methanol-water (100 mL), containing 10% palladium-on-carbon (2.6 g) was stirred overnight at room temperature under a hydrogen atmosphere. The mixture was filtered over celite, directly onto Amberlite IR 120 (Na+) cation exchange resin, and the solids thoroughly washed with aqueous methanol. The mixture was stirred with the resin for about 1 h, filtered and concentrated. Examination of this material by mass spectrometry indicated that it was contaminated with a small proportion of a compound carrying a benzoyl group, as evidenced by an ion with a mass of 783 (M-Na+Bz). This material was again subjected to Zemplen trans-esterification exactly as aforedescribed. After the usual processing, it was purified on a silica gel column (13:6:1 chloroform-methanol-water). Fractions corresponding to the product were pooled and concentrated to yield a residue, which was redissolved in water, filtered (0.2 μM Cellulose acetate syringe filter) and lyophilized to yield 26 (1.68 g, 89.8%), as a white fluffy solid; $[\alpha]_D$ −58.6° (c 0.7, methanol), t.l.c. (13:6:1 chloroform-methanol-water); negative LSIMS: 679.6 (M-Na)−, 701.7 (M-H)−.

EXAMPLE 23

Preparation of Octyl O-(2,6-di-O-benzoyl-3,4-O-isopropylidene -β-D-galactopyranosyl-(1→4)-2,3,6-tri-O-benzoyl-β-D-glucopyranoside (27)

A solution of 1.9 (2.5 g, 5 mmol) in pyridine (50 mL), was treated with benzoyl chloride (4.5 mL, 37.5 mmol) and the mixture stirred overnight at room temperature. The mixture was poured into ice-water and extracted with dichloromethane (3×30 mL). The combined organic layer was washed with water, cold 5% $H_2SO_4$, cold saturated $NaHCO_3$, and water, dried, and concentrated to a syrup, which crystallized from methanol to yield 27 (4.7 g, 91.6%); m.p. 156°–157° C.; $[\alpha]_D$ +40.50 (C 1.3, chloroform), t.l.c. (8.5:1.5 toluene-ethyl acetate). $^1H$ NMR ($CDCl_3$): δ8.40–7.20 (m, 25 H, arom.), 5.72 (t, 1H, J 9.4 Hz, H-3), 5.42 (dd, 1H, J 7.9 and 9.7 Hz, H-2'), 5.14 (t, 1 H, J 7.3 Hz, H-2'), 4.64 (d, 1 H, J 7.9 Hz, H-1'), 4.58 (d, 1 H, J 7.7 Hz, H-1), 1.52, 1.24 (s, 3 H each, [$(CH_3)_2C$], and 0.8 [t, 3 H, J 7.1 Hz, $CH_3(CH_2)_6$]; $^{13}C$ NMR ($CDCl_3$): δ166.57, 166.49, 166.24, 165.76, 165.49 (5×PhCO), 111.45 [$C(CH_3)_2$], 101.74, 100.74 (C-1, C-1'), 77.68 (C-4), 76.04–71.93 (C-2, 2', C-3,3', C-4', C-5,5'), 70.90 [$OCH_2(CH_2)_6$], 63.43, 63.28 (C-6, C-6'), 32.25–23.16 [$CH_2)_6CH_3$], 28.01, 26.74 [$C(CH_3)_2$], and 14.65 ($CH_3$); negative LSIMS: 1167.4 (M+mNBA)−, positive LSIMS: 1037.0 (M+Na)+.

EXAMPLE 24

Preparation of Octyl O-(2,6-di-O-benzoyl-β-D-galactopyranosyl) -(1→4)-2,3,6-tri-O-benzoyl-β-glucopyranoside (28)

A solution of compound 27 (4.5 g) in chloroform (200 mL) was treated with trifluoroacetic acid (25 mL) and water (3 mL), and the mixture stirred for 2 h at room temperature. The mixture was washed with ice-cold, saturated $NaHCO_3$, and water, dried and concentrated to yield 28 (4.15 g, 96%), amorphous; $[\alpha]_D$ +38.60 (c 1.6, chloroform), t.l.c. (4:1 toluene-ethyl acetate). $^{13}C$ NMR ($CDCl_3$): δ166.69–165.78 (5×PhCO), 101.75, 101.51 (C-1, C-1'), 77.06 (C-4), 70.86 [$OCH_2(CH_2)_6$], 63.37, 62.86 (C-6, C-6'), 32.26–23.16 [$(CH_2)_6CH_3$], and 14.66 ($CH_3$); negative LSIMS: 973.3 (M-H)−, 1019.9 (M+NO2)−, 1127.1 (M+mNBA)−, positive LSIMS: 997.0 (M+Na)+.

EXAMPLE 25

Preparation of Octyl O-(4-O-acetyl-2,6-di-O-benzoyl -β-D-galactopyranosyl-(1→4)-2,3,6-tri-O-benzoyl-β-D-glucopyranoside (29)

A solution of 28 (4 g) in a 1:1 mixture of benzene and triethylorthoacetate (100 mL), containing 4-toluenesulfonic acid (200 mg), was stirred for 1 h at room temperature. The acid was neutralized with triethylamine and the mixture concentrated, dissolved in 80% aqueous acetic acid and stirred for 40 min at room temperature. The acetic acid was evaporated in vacuo, and co-evaporated with toluene to yield 29 (4 g, 95.9%); $[\alpha]_D$ +17.85° (c 1.35, chloroform). $^{13}C$ NMR ($CDCl_3$): δ171.25 ($CH_3CO$), 166.85–165.78 (5×PhCO), 101.73, 101.06 (C-1, C-1'), 76.34 (C-4), 70.92 [$OCH_2-(CH_2)_6$], 63.34, 61.96 (C-6, C-6'), 32.25–21.19 [$(CH_2)_6CH_3$], and 14.63 ($CH_3$); Negative LSIMS: 1169.0 (M+mNBA)−, 1038.8 (M+Na)+.

EXAMPLE 26

Preparation of Octyl 4-O-(sodium β-D-galactopyranosyl 3-sulfate)-β-glucopyranoside (31)

A mixture of 29 (3.8 g) and sulfurtrioxide-pyridine complex (3.8 g) in pyridine (60 mL) was stirred for about 40 min at 55°–60° C. The mixture was cooled to room temperature, methanol (5 mL) was added and the mixture stirred for 20 min at room temperature. It was concentrated and co-evaporated with toluene. The residue was purified on a silica gel column (19:1 and 9:1 (v/v) chloroform-methanol) to yield 30 (3.5 g, 83.3%); negative LSIMS: 1095.2 (M-Na)−.

Compound 30 was dissolved in methanol (100 mL) containing a catalytic amount of sodium methoxide and the mixture stirred overnight at about 45°–50° C. After processing in the usual manner, the residue was purified on a silica gel column (13:6:1 chloroform-methanol-water) to yield 31 (1.65 g, 94.8%); −4.5° (c 1.5, methanol); Negative LSIMS: 533.4 (M+Na)−, 555.4 (M-H)−.

EXAMPLE 27

Selectin Ligand Properties of Lactose Derivatives

Compounds 13a, 13b, 26 and 31 were tested for their capacity to bind to E, L and P selectin. The ELISA assay used consists of evaporating 2,3 sLex glycolipid, at 25 picomoles per well, onto microtiter wells, and then washing the excess off with water. The wells are blocked with 5% BSA at room temperature for an hour and then washed with PBS containing 1 mM Ca. While the plate is being blocked, biotin labelled goat $F(ab')_2$ IgG (Fc specific) and streptavidin-alkaline phosphatase diluted 1:1500 in 1% BSA-PBS (1 mM Ca) are combined with either the E, L or P Selectin-lgG chimera (L91-10) at 200 ng/mL and incubated at 37° C. for 15 minutes to allow a complex to form. This provides a soluble "multivalent" receptor. Compounds 13a and 13b were added at final concentrations ranging from 1.5 to 5.0 mM to the soluble receptor and allowed to react at 37° C. for 45 minutes. The solutions were then placed in the microtiter wells that had been washed after being blocked, and the plates incubated at 37° C for 45 minutes to allow the soluble receptor to bind to the known natural ligand, 2,3 sLex glycolipid. The positive control was the signal produced by soluble "multivalent" receptor reacted with only the ligand evaporated to the microtiter well. This was considered "100% binding." The signal produced by receptor previously reacted with inhibitor is divided by the signal produced by the positive control, multiplied by 100, to calculate % receptor bound in the presence of the inhibitor. The reciprocal of this is % inhibition.

It is apparent from Table 1 that compounds 13a, 13b and 26 inhibit binding of E selectin to 2,3 sLex glycolipid. Over the three concentrations tested 13b was the better inhibitor with the greatest difference apparent at 5 mM concentration. At this concentration 13b showed 82.5% inhibition compared to 48% for 13a.

TABLE 1

| INHIBITION OF E-SELECTIN BINDING TO sLeX | | |
|---|---|---|
| COMPOUND | CONC. (mM) | % INHIBITION |
| 13a | 1.25 | 30 |
|  | 2.5 | 34 |
|  | 5.0 | 48 |
| 13b | 1.25 | 48.5 |
|  | 2.5 | 45.4 |
|  | 5.0 | 82.5 |

TABLE 1-continued

INHIBITION OF E-SELECTIN BINDING TO sLeX

| COMPOUND | CONC. (mM) | % INHIBITION |
|---|---|---|
| 26 | 0.5 | 0 |
|  | 1.0 | 30 |
|  | 2.0 | 50 |
|  | 4.0 | 70 |
| 31 | 0.5 | 0 |
|  | 1.0 | 0 |
|  | 2.0 | 0 |
|  | 4.0 | 0 |

It is apparent from Table 2 that both compounds 13a and 13b also inhibit binding of L selectin to 2,3 sLex glycolipid. However, the difference here was considerably greater than the difference in % inhibition for binding to E selectin. For example, at 1.25 mM, 13b surprisingly showed 90% inhibition. 100% inhibition was observed at 2 mM and 5 mM. In marked contrast, 13b displayed only 13% inhibition at 1.25 mM and a maximum inhibition of 47% at 5 mM. Compound 26 displayed 30% inhibition at all the concentrations tested. Compound 31 is inactive in the inhibition of E- and L-selectin binding to sLex.

TABLE 2

INHIBITION OF L-SELECTIN BINDING TO sLeX

| COMPOUND | CONC. (mM) | % INHIBITION |
|---|---|---|
| 13a | 1.25 | 13 |
|  | 2.5 | 27 |
|  | 5.0 | 47 |
| 13b | 1.25 | 90 |
|  | 2.5 | 100 |
|  | 5.0 | 100 |
| 26 | 0.5 | 0 |
|  | 1.0 | 30 |
|  | 2.0 | 30 |
|  | 4.0 | 30 |
| 31 | 0.5 | 0 |
|  | 1.0 | 0 |
|  | 2.0 | 0 |
|  | 4.0 | 0 |

Table 3 indicates that compound 26 is a better inhibitor of P selectin (as compared to L-selectin) binding to 2,3 sLex glycolipid.

TABLE 3

INHIBITION OF P-SELECTIN BINDING TO sLex

| COMPOUND | CONC. (mM) | % INHIBITION |
|---|---|---|
| 26 | 0.5 | 0 |
|  | 1.0 | 20 |
|  | 2.0 | 40 |
|  | 4.0 | 45 |

EXAMPLE 28

Acute Lung Injury Assay

Experiments were done to determine the effectiveness of compounds 13b or 31 in their ability to reduce neutrophil-dependent injury to the lung endothelium and alveolar epithelium following acid aspiration injury.

Female New Zealand White rabbits (1 each/group, approx. 2 KG each) were anesthetized with halothane and ventilated with positive pressure ventilation supplemented with oxygen. Vascular catheters were placed in the carotid artery, into the internal jugular vein, and a tracheostomy was made for positive pressure ventilation. A low pH solution (HCI, pH 1.5) was installed in Ringer's lactate (osmolality= approximately 100) at a dose of 3 ml/kg into the trachea to stimulate a gastric aspiration induced lung injury. Compound 13b or 31 were injected (10 mg/kg/hr IV) 5 minutes prior to intratracheal instillation of the low pH solutions continued by hourly injections until the end of the experiment. Appropriate controls were used. An intravascular as well as an intra-alveolar radiolabelled protein tracer was injected to quantify lung endothelial and alveolar epithelial protein permeability. Arterial blood gases, systemic blood pressure and airways were monitored. At the end of 6 hours the lungs were removed and alveolar fluid was sampled from both lungs in order to measure the concentration of native protein as well as radiolabelled proteins in the airspaces to calculate lung vascular and lung epithelial permeability. Also, one lung was lavaged in order to count the neutrophils that are present in the airspaces of the lungs. Extravascular lung water measurements was done on the lung which was not lavaged. Histological sample were taken from selected portions of the lung.

Figure 2:
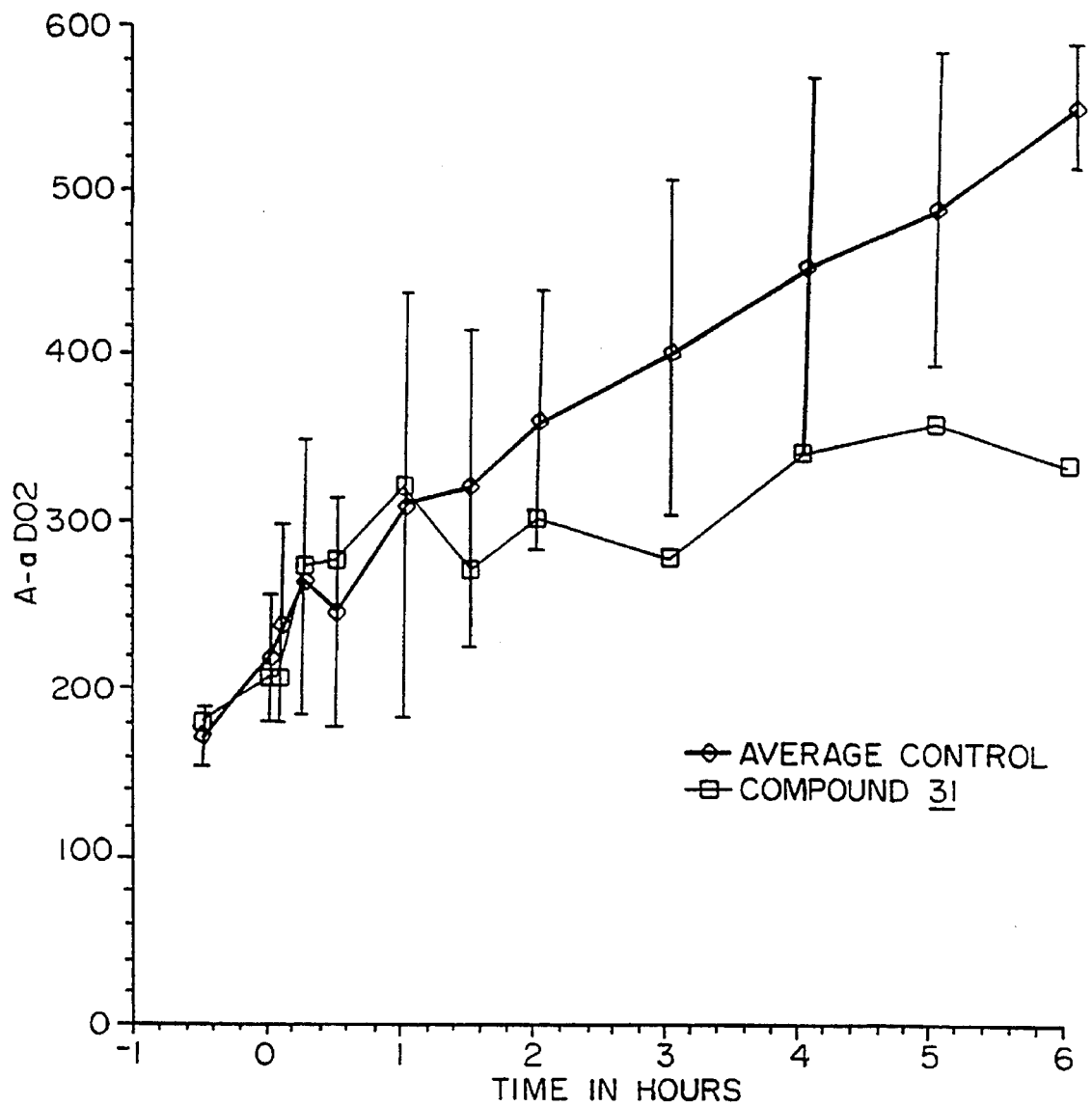
FIG. 2 shows the effect of compound 31 on rabbits in the acute lung injury model.

Animals treated with either compound 13b or 31 showed a decrease in Alveolar-arterial blood oxygen gradient as compared to the control animals. FIGS. 1 and 2 show the effect of compounds 13b and 31 respectively on rabbits in the acute lung injury model.

It is noteworthy that compound 31 (see Example 27) was inactive in vitro in inhibition of E- and L-selectin binding to sLex, but effectively reduced neutrophil-dependent injury to the lung endothelium and alveolar epithelium following acid aspiration injury in the acute lung injury model. It is possible that compound 31 is fucosylated in vivo, thereby explaining the positive activity of compound 31 in the acute lung injury model.

EXAMPLE 29

Reperfusion Injury Assay

Experiments were done to determine the effectiveness of compound 13b in decreasing adhesion of human neutrophils in the rabbit isolated heart. Addition of the human plasma to the rabbit isolated heart results in activation of the complement components found within the plasma, which in turn promotes an increase in the neutrophil accumulation. This model is used to determine the effect of lactose derivatives on inhibiting complement-induced neutrophil adhesion.

Hearts from New Zealand White rabbits were excised, mounted on a modified Langendorff apparatus and perfused with Krebs-Heinseleit buffer. Cardiac functional parameters were monitored upon a Grass Model 79D polygraph machine. 4% normal human plasma (NHP) was added to the recirculating buffer. Ten minutes after the addition of the plasma, 13b (0.1 mg/ml) was added to the perfusate. After 15 minutes of perfusion with the plasma, 51-chromium labelled human neutrophils ($1\times10^5$/ml) were added to the perfusate and allowed to recirculate for an additional 15 minutes. At the end of this time the hearts were washed with fresh buffer to remove non-specifically bound neutrophils, dried and counted in a well type gamma-counter. A concentration response curve was generated using concentrations of 0.001, 0.01 and 0.1 mg/ml. Six hearts were used for each of these concentrations.

Figure 3:
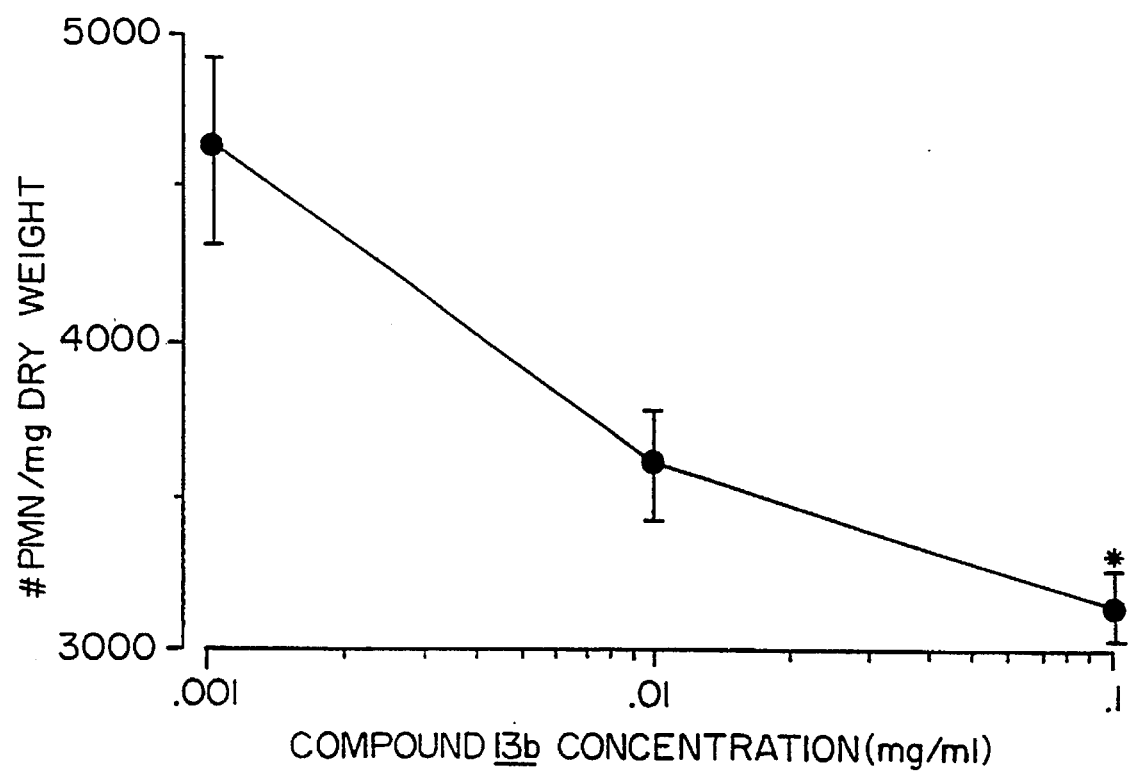
FIG. 3 shows the results of the dose response of compound 13b in the reperfusion assay. The results are expressed as the number of radiolabelled human neutrophils/ mg of dry weight of the heart.

Table 4 lists the results, expressed as the percent inhibition of neutrophil accumulation. The results of the concentration-response study are shown in FIG. 3. These results are expressed as the number of radiolabelled human neutrophils/mg of dry weight of the head.

It should be noted that the number of neutrophils seen with the 0.001 mg/ml concentration of compound 13b is similar to that of the control. Compound 13b inhibited neutrophil adhesion in a concentration-dependent manner with the most significant degree of inhibition using the 0.1 mg/ml dose. These data provide evidence that compound 13b was successful in decreasing neutrophil adhesion in this model. It should also be noted that the greatest degree of inhibition seen using pharmacological agents, including a number of peptides derived form P-selectin and antibodies directed against P-selectin and the CD11b/CD18 complex (Ma, Xin-liang, et al., *Circulation* (1993) 88-2:649), has been 40%. Compound 13b provides a degree of inhibition similar to any of the pharmacological agents tested thus far.

Based on the above results, it is apparent that the compounds of the invention are useful for treating diseases, preferably diseases that have an inflammatory component, Adult Respiratory Distress Syndrome (ARDS), ischemia and reperfusion injury, including strokes, mesenteric and peripheral vascular disease, organ transplantation, and circulatory shock (in this case many organs might be damaged following restoration of blood flow).

TABLE 4

| Compound | % Neutrophil Inhibition |
| --- | --- |
| 13b | 35 |

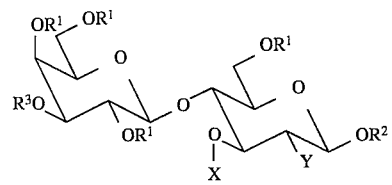

wherein each $R^1$ is independently H or lower alkyl (1–4C);

$R^2$ is H, a lower alkyl group (1–4C), an additional saccharide residue;

$R^3$ is a negatively charged moiety selected from the group consisting of $-SO^{1-}_3$ and $-PO_3^{1-}$;

Y is H, OH or lower alkyl (1–4C); and

X is H, $-CHR^4(CHOR^1)_2CHR^5OR^1$ wherein $R^4$ and $R^5$ are each independently H or lower alkyl (1–4C), 6-methyl-3,4,5-trihydroxypyran-2-yl,
6-acetyl-3,4,5,trihydroxypyran-2-yl,
6-propylamido-3,4,5,trihydroxypyran-2-yl,
6-propylamido-2,3,4-trimethoxypyran-2-yl,
6-ethyl-2,3-dihydroxy-4-methoxypyran-2-yl,
6-N-ethylamino-2-hydroxy-3,4-ethoxypyran-2-yl,
3,4,5-tri-n-propyloxypyran-2-yl,
3,4,5-trihydroxypyran-2-yl,
2,3,4-trimethoxyfuran-2-yl,
2,3-dihydroxy-4-methoxyfuran-2-yl,
2-hydroxy-3,4-ethoxyfuran-2-yl,
3,4,5-tri-n-propyloxyfuran-2-yl,
3,4,5-trihydroxyfuran-2-yl,

We claim:

1. A compound of the formula:

or 2,3,4-trihydroxybenzoyl, wherein if X is H then $R^2$ is a higher alkyl group;

and salts thereof.

2. The compound of claim 1 wherein all $R^1$ are H.

3. The compound of claim 1 wherein $R^2$ is H.

4. The compound of claim 1 wherein $R^2$ is —$CH_2(CH_2)_6CH_3$.

5. The compound of claim 1 wherein Y is H or OH.

6. The compound of claim 1 wherein X is —$CH_2(CHOH)_3H$, 2,3,4-trihydroxybenzoyl, or is a 3,4,5-trihydroxy or 3,4,5-trimethoxypyran-2-yl or furan-2-yl.

7. The compound of claim 1 wherein one of $R^4$ and $R^5$ is H and the other is H, lower alkyl (1–4C), or phenyl.

8. The compound of claim 7 wherein one of $R^4$ or $R^5$ is a methyl group.

9. The compound of claim 7 wherein both $R^4$ and $R^5$ are H.

10. The compound of claim 1 wherein all $R^1$ are H, $R^2$ is H, $R^3$ is $SO_3^{1-}$ and X is a fucosyl residue.

11. The compound of claim 1 wherein all $R^1$ are H, $R^2$ is —$CH_2(CH_2)_6CH_3$, $R^3$ is $SO_3^{1-}$ and X is a fucosyl residue.

12. The compound of claim 1 wherein all $R^1$ are H, $R^2$ is —$CH_2(CH_2)_6CH_3$, $R^3$ is $SO_3^{1-}$, and X is H.

13. The compound of claim 1 wherein $R^3$ is —$SO_3^{1-}$ and X is a fucosyl residue.

14. The compound of claim 13 wherein all $R^1$ are H and $R^2$ is —$CH_2CH_2SiMe_3$.

* * * * *

UNITED STATES PATENT AND TRADEMARK OFFICE
CERTIFICATE OF CORRECTION

PATENT NO. : 5,591,835
DATED : January 7, 1997
INVENTOR(S) : Saeed A. ABBAS et al.

It is certified that error appears in the above-identified patent and that said Letters Patent is hereby corrected as shown below:

Column 20, line 27, after "solid;" insert -- [α]D --.

Column 23, line 36, delete "-C" and insert -- $^{13}C$ --.

Claim 1, column 32, line 11: after "(1-4C)," insert -- a higher alkyl group (5-15C), alkylaryl or --.

Claim 6, column 33, lines 6-8: delete the entire claim and insert -- The compound of claim 1 wherein X is $-CH_2(CHOH)_3H$, 2,3,4-trihydroxybenxoyl, 3,4,5-trihydroxypyran-2-yl, 3,4,5-trihydroxyfuran-2-yl, 3,4,5-trimethoxypyran-2-yl or 3,4,5-trimethoxyfuran-2-yl. -- .

Signed and Sealed this

First Day of December, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 31 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

GGTGCGGCCG CGGCCAGAGA CCCGAGGAGA G 31

( 2 ) INFORMATION FOR SEQ ID NO:2:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

GGTGTCGACC CCACCTGAGA GATCCTGTG 29